US007962291B2

(12) United States Patent
Williams et al.

(10) Patent No.: US 7,962,291 B2
(45) Date of Patent: Jun. 14, 2011

(54) METHODS AND COMPUTER SOFTWARE FOR DETECTING SPLICE VARIANTS

(75) Inventors: Alan Williams, Albany, CA (US); Simon Cawley, Oakland, CA (US); John E. Blume, Sunnyvale, CA (US); Hui Wang, San Bruno, CA (US); Tyson Clark, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 725 days.

(21) Appl. No.: 11/538,054

(22) Filed: Oct. 2, 2006

(65) Prior Publication Data
US 2007/0148667 A1 Jun. 28, 2007

Related U.S. Application Data

(60) Provisional application No. 60/722,742, filed on Sep. 30, 2005.

(51) Int. Cl.
G06F 19/00 (2006.01)
C12N 15/11 (2006.01)
(52) U.S. Cl. ........................................ 702/20; 536/24.3
(58) Field of Classification Search .................... None
See application file for complete search history.

(56) References Cited

U.S. PATENT DOCUMENTS

| | | |
|---|---|---|
| 5,057,410 A | 10/1991 | Kawasaki et al. |
| 5,474,796 A | 12/1995 | Brennan |
| 5,556,749 A | 9/1996 | Mitsuhashi et al. |
| 5,571,639 A | 11/1996 | Hubbell et al. |
| 5,700,683 A | 12/1997 | Stover et al. |
| 5,795,716 A | 8/1998 | Chee et al. |
| 5,800,992 A | 9/1998 | Fodor et al. |
| 5,830,665 A | 11/1998 | Shuber et al. |
| 5,914,267 A | 6/1999 | Mertz et al. |
| 6,040,138 A | 3/2000 | Lockhart et al. |
| 6,043,080 A | 3/2000 | Lipshutz et al. |
| 6,090,553 A | 7/2000 | Matson |
| 6,287,768 B1 | 9/2001 | Chenchik et al. |
| 6,309,822 B1 | 10/2001 | Fodor et al. |
| 6,316,193 B1 | 11/2001 | He et al. |
| 6,342,355 B1 | 1/2002 | Hacia et al. |
| 6,403,309 B1 | 6/2002 | Iris et al. |
| 6,495,320 B1 | 12/2002 | Lockhart et al. |
| 6,548,257 B2 | 4/2003 | Lockhart et al. |
| 6,600,996 B2 | 7/2003 | Webster et al. |
| 6,812,005 B2 | 11/2004 | Fan et al. |
| 6,927,032 B2 | 8/2005 | Lockhart et al. |
| 7,089,121 B1 | 8/2006 | Wang |
| 7,109,390 B2 | 9/2006 | Lyznik et al. |
| 7,217,521 B2 | 5/2007 | Qian |
| 7,341,835 B2 | 3/2008 | Blume et al. |
| 2002/0048763 A1 | 4/2002 | Penn et al. |
| 2003/0186296 A1 | 10/2003 | Fodor et al. |
| 2004/0009512 A1 | 1/2004 | Ares et al. |
| 2004/0014107 A1 | 1/2004 | Garcia-Blanco et al. |
| 2004/0234963 A1 | 11/2004 | Sampas et al. |
| 2005/0214824 A1 | 9/2005 | Balaban |
| 2005/0244851 A1 * | 11/2005 | Blume et al. ..................... 435/6 |
| 2006/0141506 A1 | 6/2006 | Balaban |
| 2006/0281126 A1 | 12/2006 | Wang |

FOREIGN PATENT DOCUMENTS

| | | |
|---|---|---|
| WO | WO 97/10365 | 3/1997 |
| WO | WO 98/30883 | 7/1998 |
| WO | WO 01/57252 | 8/2001 |
| WO | WO 01/81632 | 11/2001 |
| WO | WO 02/16650 | 2/2002 |
| WO | WO 02/090516 | 11/2002 |
| WO | WO 03/014295 | 2/2003 |

OTHER PUBLICATIONS

Hu et al. Predicting Splice Variant from DNA Chip Expression Data Genome Research vol. 11, pp. 1237-1245 (2001).*
Clark et al. Genomewide Analysis of mRNA Processing in Yeast Using Splicing-Specific Microarrays. Science vol. 296 pp. 907-910 (2002).*
Moody et al. Cross-species hybridisation of pig RNA to human nylon microarrays BMC Genomics vol. 3, article 27 (2002).*
Lee et al. Analysis of alternative splicing with microarrays: successes and challenges Genome Biology vol. 5, article 231 (2004).*
U.S. Appl. No. 09/697,877, filed Oct. 26, 2000, Balaban.
U.S. Appl. No. 10/384,275, filed Mar. 6, 2003, Wang et al.
U.S. Appl. No. 11/069,720, filed Feb. 28, 2005, Cline et al.
Adams et al., "ZNF265—a novel spliceosomal protein able to induce alternative splicing," *The Journal of Cell Biology*, 154(1):25-32 (Jul. 2001).
Affymetrix GeneChip® Exon Array Whitepaper Collection, "Alternative Transcript Analysis Methods for Exon Arrays," rev. Oct. 11, 2005, ver. 1.1. http://media.affymetrix.com/support/technical/whitepapers/exon_alt_transcript_analysis_whitepaper.pdf.
Affymetrix GeneChip® Exon Array Whitepaper Collection, "Exon Array Background Correction," rev. Sep. 27, 2005, ver. 1.0. http://media.affymetrix.com/support/technical/whitepapers/exon_background_correction_whitepaper.pdf.
Affymetrix GeneChip® Exon Array Whitepaper Collection, "Exon Probeset Annotations and Transcript Cluster Groupings," rev. Sep. 27, 2005, ver. 1.0. http://media.affymetrix.com/support/technical/whitepapers/exon_probeset_trans_clust_whitepaper.pdf.
Affymetrix GeneChip® Exon Array Whitepaper Collection, "Gene Signal Estimates from Exon Arrays," rev. Sep 27, 2005, ver. 1.0. http://www.affymetrix.com/support/technical/whitepapers.affx.
Ahern, H., "Biochemical, reagent kits offer scientists good return on investment," *The Scientist*, 1995, 9(15):20-22.
Black, Douglas L., "Protein Diversity from Alternative Splicing: A Challenge for Bioinformatics and Post-Genome Biology," *Cells*, 103:367-370 (Oct. 27, 2000).

(Continued)

Primary Examiner — John S Brusca
(74) Attorney, Agent, or Firm — Sandra E. Wells; Thomas J. Siepmann; Steven M. Yee

(57) ABSTRACT

Methods and software products for analysis of alternative splicing are disclosed. In general the methods involve normalizing probe set or exon intensity to an expression level measurement of the gene. The methods may be used to identify tissue-specific alternative splicing events.

12 Claims, 19 Drawing Sheets

OTHER PUBLICATIONS

Chetverin et al., "Oligonucleotide Arrays: New Concepts and Possibilities," *Bio/Technology*, Nature Publishing Co., NY, U.S., vol. 12, pp. 1093-1099 (Nov. 1994).

Florea et al., "A computer program for aligning a cDNA sequence with a genomic DNA sequence," *Genome Research*, Sep. 1998, 8(9):967-974.

Gelfand et al., "Gene recognition via spliced sequence alignment," *Proc. Nat'l. Acad. Sci. U.S.A.*, Aug. 20, 1996, 93(17):9061-9066.

Gerke et al., "A protein associated with small nuclear ribonucleoprotein particles recognizes the 3' splice site of premessenger RNA," *Cell*, 47(6):973-984 (1986).

Johnson et al., "Genome-Wide survey of Human alternative Pre-mRNA splicing with exon junction microarrays," *Science*, 302:2141-2144 (Dec. 2003).

Kafasla et al., "Association of the 72/74-kDa proteins, members of the heterogeneous nuclear ribonucleoprotein M group, with the pre-mRNA at early stages of spliceosome assembly;" *Biochemical Journal*, 363 (Pt 3):793-799 (2002).

Kamma et al., "Molecular characterization of the hnRNP A2/B1 proteins: Tissue-specific expression and novel isoforms," *Experimental Cell Research*, 246(2):399-411 (1999).

Kan, et al., "Gene structure prediction and alternative splicing analysis using genomically aligned ESTs," *Genome Research*, May 2001, 11(5):889-900.

Kapranov et al., "Large-scale transcriptional activity in chromosomes 21 and 22," *Science*, May 3, 2002; 296(5569):916-919.

Kikuchi et al., "Expression profiles of non-small cell lung cancers on cDNA microarrays: Identification of genes for prediction of lymph-node metastasis and sensitivity to anti-cancer drugs," *Oncogene* 22:2192-2205 (2003).

Le Hir et al., "Pre-mRNA splicing alters mRNP composition: evidence for stable association of proteins at exon-exon junctions," *Genes & Development*, 14(9):1098-1108 (May 2000).

Lee C et al., "ASAP: The Alternative Splicing Annotation Project," *Nucleic Acid Res.*, 31(1):101-5, 2002.

Li and Wong, "Model-Based Analysis of Oligonucleotide Arrays: Expression Index Computation and Outlier Detection," *Proc. Natl. Acad. Sci.*, (2001) 98(1):31-36.

Lopato et al., "Pre-mRNA splicing in plants : characterization of Ser/Arg splicing factors," *Proc. Nat'l. Acad. Sci. U.S.A.*, 93:3074-3079 (1996).

Mironov et al., "Performance-guarantee gene predictions via spliced alignment," *Genomics*, 51:332-339, 1998.

Niranjanakumari et al., "Reversible cross-linking combined with immunoprecipitation to study RNA-protein interactions in vivo," *Methods*, 26:182-190 (2002).

Rychlik, Wojciech and Rhoads, Robert E., "A computer program for choosing optimal oligonucleotides for filter hybridization, sequencing and in vitro amplification of DNA," *Nucleic Acids Research*, 17(21):8543-8551, 1989.

Schaal et al., "Selection and characterization of pre-mRNA splicing enhancers: identification of novel SR protein-specific enhancer sequences," *Molecular and Cellular Biology*, 19(3):1705-1719 (1999).

Schena et al., "Quantitative Monitoring of Gene Expression Patterns with a Complementary DNA Microarray," *Science*, 270(5235):467-470 (Oct. 1995).

Shoemaker et al., "Experimental Annotation of the Human Genome Using Microarray Technology," *Nature*, 409(6822):922-927 (Feb. 15, 2001).

Tenenbaum et al., "Identifying mRNA subsets in messenger ribonucleoprotein complexes by using cDNA arrays," *Proc. Nat'l. Acad. Sci. U.S.A.*, 97(26):14085-14090 (Dec. 2000).

UCSC Genome Bioinformatics, <www.genome.uscs.edu/FAQ/FAQreleases>, pp. 1-10, Sep. 17, 2006.

Wang et al., "Gene Structure-Based Splice Variant Deconvolution Using a Microarray Platform," *Bioinformatics*, (2003) vol. 19 Suppl. 1: i315-i322.

Zahler et al., "SR Proteins: A Conserved Family of Pre-mRNA Splicing Factors," *Genes & Development*, 6:837-847 (1992).

\* cited by examiner

Mean-square error for background

METHODS AND COMPUTER SOFTWARE FOR DETECTING SPLICE VARIANTS

RELATED APPLICATIONS

The present application claims priority to U.S. Provisional Application No. 60/722,742, filed Sep. 30, 2005, the disclosure of which is incorporated herein by reference in its entirety.

FIELD OF THE INVENTION

The invention is related to computer methods to identify differential splicing events. Specifically, this invention provides methods, computer software products and systems for analysis of microarray data to identify differentially spliced exons.

BACKGROUND OF THE INVENTION

Recent genome-wide analysis of alternative splicing indicates that a large portion of human genes, probably more than half, have alternative splice forms. Alternative splicing provides the cell with a mechanism to generate multiple gene products from the same transcript, adding to the functional complexity of the genome. Regulated alternative splicing may be used to create different proteins under different circumstances, allowing production of functionally related but distinct proteins and thus expanding the protein-coding potential of genes and genomes.

The identities of the genes that are being expressed in a biological sample at any given time and the amount of expression of those genes provide a gene expression profile for that sample. The gene expression profile is an indication of the status of that sample. For example, different tissue types will have different gene expression profiles reflecting the expression of different genes and differences in the spliced forms of individual genes. Differences in expression profile may also be observed between samples from the same tissue type when one sample is diseased. High-throughput methods to analyze and detect expression of alternative splice forms, characterization of alternative splicing, and regulation of alternative splicing are an important research focus.

SUMMARY OF THE INVENTION

Computer software products and methods for analysis of alternative splicing are disclosed.

BRIEF DESCRIPTION OF THE DRAWINGS

FIG. 8: (Rule 2a) The arrows indicate a shared splice site between the two extended annotations. The bottommost extended annotation is joined with the cluster that it shares a splice site with.

Figure 1:
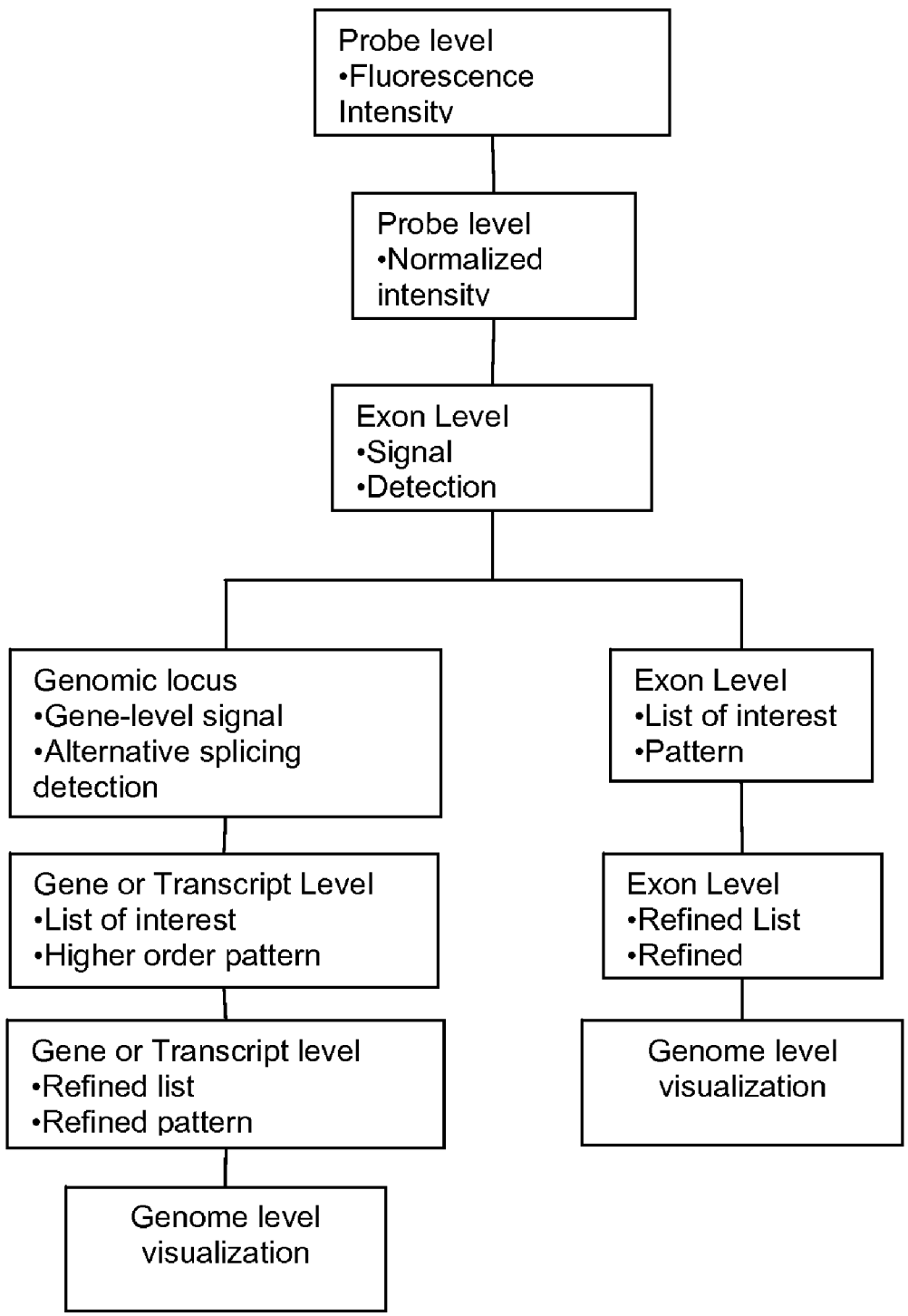
FIG. 1: Schematic of Exon Array data analysis workflow.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, N.Y., N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675, each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5, 413,909, 5,861, 245) and nucleic acid based sequence amplification (NABSA). (See, U.S. Pat. Nos. 5,409,818, 5,554,517, and 6,063,603, each of which is incorporated herein by reference). Other amplification methods that may be used are described in U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. No. 6,361,947, 6,391,592 and U.S. Ser. Nos. 09/916,135, 09/920,491 (U.S. Patent Application Publication 20030096235), 09/910,292 (U.S. Patent Application Publication 20030082543), and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davis, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), 10/065,856, 10/065,868, 10/328,818, 10/328,872, 10/423,403, and 60/482,389 and U.S. Patent Publication No. 20040049354.

b) Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "array plate" as used herein refers to a body having a plurality of arrays in which each microarray is separated by a physical barrier resistant to the passage of liquids and forming an area or space, referred to as a well, capable of containing liquids in contact with the probe array.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes refer by "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a bioplyomer is a "biomonomer".

The term "cartridge" as used herein refers to a body forming an area or space referred to as a well wherein a microarray is contained and separated from the passage of liquids.

The term "clamping plate" as used herein refers to a device used for fastening two or more parts.

The term "combinatorial synthesis strategy" as used herein refers to an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, and then illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "effective amount" as used herein refers to an amount sufficient to induce a desired result.

The term "excitation energy" as used herein refers to energy used to energize a detectable label for detection, for example illuminating a fluorescent label. Devices for this use include coherent light or non coherent light, such as lasers, UV light, light emitting diodes, an incandescent light source, or any other light or other electromagnetic source of energy having a wavelength in the excitation band of an excitable label, or capable of providing detectable transmitted, reflective, or diffused radiation.

The term "gaskets or o-ring" as used herein refers to any of a wide variety of seals or packings used between joined parts to prevent the escape of a gas or fluid. Gaskets or o-rings can be made of materials such as elastomer.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations.

For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "isolated nucleic acid" as used herein means an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

"Labeled moiety" refers to a moiety capable of being detected by the various methods discussed herein or known in the art.

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "microtiter plates" as used herein refers to arrays of discrete wells that come in standard formats (96, 384 and 1536 wells) which are used for examination of the physical, chemical or biological characteristics of a quantity of samples in parallel.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "reader" or "plate reader" as used herein refers to a device which is used to identify hybridization events on an array, such as the hybridization between a nucleic acid probe on the array and a fluorescently labeled target. Readers are known in the art and are commercially available through Affymetrix, Santa Clara Calif. and other companies. Generally, they involve the use of an excitation energy (such as a laser) to illuminate a fluorescently labeled target nucleic acid that has hybridized to the probe. Then, the reemitted radiation (at a different wavelength than the excitation energy) is detected using devices such as a CCD, PMT, photodiode, or similar devices to register the collected emissions. See U.S. Pat. No. 6,225,625.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "surface" or "active probe surface" or "target surface" as used herein refers to the area of the microarray to be analyzed with reagents.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "variance" as used herein generally refers to a value that is a measure of the dispersion of data. For example, it will be appreciated by those skilled in the relevant art that, variance may be defined as the mean of the square of the differences between the samples and can be mathematically represented as:

$$\sigma^2 = \frac{\sum (X - \overline{X})^2}{n - 1}$$

where, X is equal to a particular value that could for instance be an emission intensity value for a probe feature, $\overline{X}$ is equal to the mean of all the values and n is equal to the total number of values. The mean is equal to the sum of all the observation values divided by the number of observations.

The term "wafer" as used herein refers to a substrate having surface to which a plurality of arrays are bound. In a preferred embodiment, the arrays are synthesized on the surface of the substrate to create multiple arrays that are physically separate. In one preferred embodiment of a wafer, the arrays are physically separated by a distance of at least about 0.1, 0.25, 0.5, 1 or 1.5 millimeters. The arrays that are on the wafer may be identical, each one may be different, or there may be some combination thereof Particularly preferred wafers are about 8"×8" and are made using the photolithographic process.

C. Analysis of Gene Expression on Exon Arrays

I. Alternative Transcript Analysis Methods for Exon Arrays

With exon arrays like the GeneChip® Human Exon 1.0 ST Array, researchers can examine the transcriptional profile of an entire gene. Being able to gather data for each individual exon enables the investigation of phenomena such as alternative splicing, alternative promoter usage, and alternative termination while also providing more probe level data to determine the overall rate of expression a particular locus. Methods of detecting relative changes in alternative transcript forms are disclosed herein.

An ANOVA based method based on a Splicing Index equal to the ratio of exon signal to gene signal works well in two test data sets: one a tissue panel and the other a set of cancer and normal from the same tissue. For the tissue panel data set, a correlation based method, Robust PAC, performs well. Other methods for alternative splicing analysis bases on ANOVA are disclosed in U.S. patent application No. 11/069,720.

One of the most well studied alternative splicing events is the alternative utilization of "cassette exons". The performance of different mathematical methods designed to detect alternatively spliced cassette exons from the exon array data was evaluated. First, the method's robustness was tested in an artificial data set by constructing "genes" comprised of a group of probe selection regions that are best suggested by annotation evidence as biologically real and are always jointly expressed in a sample data set. Each such group of probe selection regions is referred to as "core constitutive exons" of that "gene." The alternative splice events were simulated in each such "gene" by substituting exons from alternative regions of the genome and constructed ROC curves as a way to measure the performance of the different methods.

The data set included a set of core constitutive exons, a tissue panel and a colon cancer panel. To generate a set of exons that appear to be constitutively included in all transcripts (core constitutive exons) splicing graphs were generated as described (Sugnet, et al, Pac Symp Biocomput., p.66-77, 2004) using all human RefSeq, mRNA and EST sequences. The graphs were pruned by requiring that each exon be either also present in mouse cDNAs or present multiple times in human cDNAs. The graphs were then searched to identify exons that were constitutively included in the pruned graph. To ensure that an exon is likely to be present in all transcripts a minimum number of 5 mRNAs or 10 ESTs (or a combination of the two) had to contain the exon. Exons making up the core constitutive genes tend to be well-expressed; their median signal is greater than 10 times the median signal of background probesets in both data sets.

The tissue panel data set consists of 11 human tissue samples. The hybridization cocktail for each sample was scanned in triplicate, using three arrays per sample for a total of 33 scans. In this study we quantile normalized the triplicates together, then multiplicatively scaled the resulting scans so that they all had the same median ("median scaling". All features, whether genomic or non-genomic are included in both normalizations. The alternative splice set was generated by taking the probes of one exon in each gene (the first in each set) and substituting them into another gene. The probes of the real exon in the substituted gene were moved to yet another gene, and after repeating over all 5,800 genes, each gene had an "exon" that did not belong to it.

This approach works as variation within replicate groups is not due to biological variation and hence, if the core constitutive genes have detectable expression in one or more of the tissues, they will likely have different expression in the different tissues. Hence the alternative splice set will each contain an exon that will behave differently across tissues. The major caveat in creating this alternative splice set is that it is not clear how well this procedure mimics true biological alternative splicing behavior.

The Colon Cancer data set consists of 18 biologically distinct samples arranged in 9 pairs. Each pair is a normal colon tissue sample and a colon cancer sample from each of 9 different individuals. There are no replicate scans. All scans were normalized using median scaling. For the colon cancer set, biological variation in signal is large enough within normal and tumor groups so that around 98% of the genes did not show significant differences in means of signal between the group of cancer and normal samples (p-value >0.05). Accordingly, the approach in creating an Alternative splice set as in the tissue panel data will not work well; replacing an exon by an exon from another gene will not induce detectable signal changes from one group to the other and hence methods of alternative splice detection based on changes in signal of exon normalized by gene will not detect anything. Instead, we took a different approach: a "background" set of probesets was generated by randomly selecting 5,800 probesets from probesets with mean signal across all 18 samples less than the $45^{th}$ percentile of mean signal of each probeset across all 18 samples.

An alternative splice data set was simulated by replacing probe intensities in the first exon in each gene with probe intensities from a "background" probeset for the normal scans only. Tumor scans were left untouched. We matched the number of probes in the replacement exon, as PLIER (PLIER: An M-Estimator for Expression Array, Hubbell, E. Affymetrix White Paper, 2005) signal is calculated across all samples by using probe intensities. Replacement probes need not have the same GC content, and replacement probe intensities in each sample were adjusted by the ratio of surrogate intensity mismatch of original to replacement based on GC content.

Exons making up the core constitutive genes have much higher overall signal than the background probesets on the chip: the median signal (2.5) of background probesets is around the $20^{th}$ percentile of all probeset signals and the median signal (35) of the first exon is around the $70^{th}$ percentile of all probeset signals.

Several different methods for splice detection are disclosed: Pattern-Based Correlation (PAC) and two ANOVA methods: Microarray Detection of Alternative Splicing (MIDAS) presented here, and ANOSVA (Cline et al, Bioinformatics 21(suppl_1):i107-i115, 2005). Their suitability to any particular data set will depend on the structure of the data set and the goals of the experiment. Data set exploration preferably uses at least two methods, including variations on the disclosed methods.

In general, preferred splice detection methods include the following features. Under the null hypothesis, exons or probes comprising a gene are assumed to be proportional to each other across different samples. A model is fit that predicts probe or exon response under the null hypothesis. A statistic is constructed that measures how deviant the data is from the model. This statistic is used to construct a p-value.

Splicing Index

A Splicing Index captures the basic metric for the analysis of alternative splicing. Specifically it is a measure of how much exon specific expression (with gene induction factored out) differs between two samples. The first step is to normalize the exon level signals to the gene level signals.

$$n_{i,j,k} = \frac{e_{i,j,k}}{g_{j,k}} \qquad \text{Equation 1:}$$

where $e_{ijk}$ is the exon signal estimate of the i exon, j experiment, and k gene. $G_{j,k}$ is the gene level signal estimate of the j experiment and k gene. The splicing index is then the ratio of normalized exon signal estimates from one sample or set of samples relative to another. For example, in the colon cancer data set a splicing index could be established for each gene by taking the median $n_{i,j,k}$ for the cancer samples and dividing by the median $n_{i,j,k}$ for the normal samples. Alternatively one might want to calculate a splicing ratio for each paired normal/cancer sample and then report the median ratio. A similar approach is described in Clark et al. *Science* 296:907-10 (2002).

The PAC approach assumes that in the absence of splicing, exon expression follows gene expressions across samples using the following model:

$$e_{i,j,k} = \alpha_{i,k} g_{j,k} \quad \text{Equation 2}$$

where $e_{i,j,k}$ is the signal of the i-th exon of the j-th sample of the k-th gene, $g_{j,k}$ is the signal of k-th gene in the j-th sample, and $\alpha_{i,k}$ is the ratio of exon i signal to its gene signal.

Preferably use a robust measure of gene signal and correlate signal of each exon with this signal. Low correlations are indications of alternative splicing. The robust measure of gene signal allows multiple exons to not track the overall gene, so long as they remain in a "small enough" minority. In preferred aspects PLIER is used.

An important class of experiments asks the following question: Is there an alternative splice variant present in one group out of two groups of samples. PAC has the problem that it will fail in two-sample cases, as correlation will always be +1 (exon response agrees in direction from one sample type to the other) or −1 (exon response disagrees in direction); this is expected to happen no matter how small the change actually is; in the rare event that there is no numerical change correlation would be zero. Hence PAC is better suited to experiments with a relatively large number of sample types.

MIDAS

In another aspect an alternative ANOVA based method based on measuring differences between exon level signal and aggregate gene level signal may be used. This method is referred to herein as Microarray Detection of Alternative Splicing or MIDAS. In general the underlying concept of MIDAS is as follows: (1) PLIER is used to generate a robust estimate of gene-level signal by using data from all features in all exons in the gene. This signal has the virtue that it will be robust against exons that exhibit anomalous signal across samples, whether they be non-expressing probe sets, probe sets that are incorrectly assigned to a gene, or are true alternative splice exons. Since this array has no mismatch probes a surrogate estimate of mismatch is generated and used by using the median intensity of all antigenomic probes on the same array that have the same GC content as the probe. (2) PLIER is used to similarly generate an estimate of signal for each exon. (3) Under the null hypothesis of no alternative splicing for an exon, the difference between the logged signal for the exon and its gene is expected to be a constant across all samples. In other words, it is expected that observed signal from each exon will have a constant ratio with observed signal from its gene.

A detection metric or statistic will preferably be based on log ratio of exon signal to gene signal, i.e, the difference between logged signal of each exon and its gene. In preferred aspects a small constant is added before logging to stabilize variance.

MIDAS Relation to ANOVA

Statistics based on the Splicing Index can be calculated either for each gene or for each exon. A model for possible splicing is:

$$e_{i,j,k} = \alpha_{i,k} p_{i,j,k} g_{j,k} \quad \text{Equation 3}$$

where $e_{i,j,k}$ is the signal of the i-th exon of the j-th sample of the k-th gene, $g_{j,k}$ is the signal of k-th gene in the j-th sample, $\alpha_{i,k}$ is the ratio of exon i signal to its gene signal in the sample where it is maximally expressed, and $0 \leq P_{i,j,k} \leq 1$ is a Splicing Index that estimates the proportionate expression of this exon of this gene in tissue j. Dividing both sides by $g_{j,k}$ to factor out effects due to gene induction and taking logs reduces this to an additive model (ignoring the possibility of zero signal):

$$\log(e_{i,j,k}/g_{j,k}) = \log(e_{i,j,k}) - \log(g_{j,k}) = \log(\alpha_{i,k}) + \log(p_{i,j,k}) \quad \text{Equation 4}$$

Exon-Level Detection vs. Gene Level Detection

Gene-level MIDAS is a 2-way ANOVA that includes an error term and possible interactions comparing:

$$\log(e_{i,j,k}) - \log(g_{j,k}) = \log(\alpha_{i,k}) + \log(p_{i,j,k}) + \gamma_{i,j,k} + \epsilon_{i,j,k} \quad \text{Equation 5}$$

to the reduced model:

$$\log(e_{i,j,k}) - \log(g_{j,k}) = \log(\alpha_{i,k}) + \epsilon_{i,j,k} \quad \text{Equation 6}$$

So we ask the question: are effects other than exon effects present; i.e., test $\log(P_{i,j,k}) = \gamma_{i,j,k} = 0$ across samples and exons.

Exon-level MIDAS considers the situation an exon at a time. In this narrow view $\log(\alpha_{i,k})$ is constant and hence it is appropriate to use classical 1-way ANOVA that compares the full model:

$$\log(e_{i,j,k}) - \log(g_{j,k}) = \log(\alpha_{i,k}) + \log(p_{i,j,k}) + \epsilon_{i,j,k} \quad \text{Equation 7}$$

to:

$$\log(e_{i,j,k}) - \log(g_{j,k}) = \log(\alpha_{i,k}) + \epsilon_{i,j,k} \quad \text{Equation 8}$$

to test the hypothesis of no alternative splicing by testing for the constant effects model $\log(P_{i,j,k}) = 0$ for all k samples.

As discussed above, the log model is inappropriate when exons or gene are not expressed. In practice, stabilizing variance by adding a constant (as we do here and further discussed below) helps to reduce the false positive rate. Both PAC and MIDAS show considerable improvement in the ROC curves when using exon-level detection over gene-level detection.

ANOSVA

A detailed description of the ANOSVA can be found in (Cline et al, 2005). In short, ANOSVA assumes all probe responses can be modeled as proportional to each other across different samples in the absence of alternative splicing; this reduces to an additive ANOVA model after taking logs. The ANOSVA method then tests for an alternative hypothesis of non-zero interactions between samples and exons using an F-statistic. Preliminary evaluation of ANOSVA on exon array data did not yield good performance for exon array data.

DECONV

Another algorithm for estimating relative concentrations of different splice variants is described in (Wang, et al, Bioinformatics 2003 19(suppl 1):i315-i322), where it is applied to data on an experimental microarray. If we define a set of splice variants each consisting of all exons but one, this algorithm can be recast into a model for probe-level intensities $x_{h,i,j,k}$ similar in form to Equation 2 above, but with an extra multiplicative term denoting the probe affinity $\alpha_{h,i,k}$ of probe h of exon i of gene k in tissue j:

$$X_{h,i,j,k} = \alpha_{h,i,k} \alpha_{i,k} p_{i,j,k} g_{j,k} + \epsilon_{h,i,j,k} \quad \text{Equation 9}$$

Parameters are estimated using an iterative maximum likelihood estimation method, including $P_{i,j,k}$. For any one gene k, the relative ratios of the $P_{i,j,k}$ across tissues j represent relative concentration estimates of exons. Alternative splicing would be present if these relative ratios deviate from each other in a statistically significant way. This model differs from MIDAS in that error is treated additively rather than multiplicatively, and gene signal is estimated directly from the MLE rather than from a separate PLIER fit.

Non-Expressing Probesets and Genes

Any Splicing Index based on the ration of exon signal to gene signal finds probesets whose response data disagrees with a model where splicing is assumed absent. However, this can occur in cases with no alternative splicing: In an exploratory array like the Human Exon Array, many probesets are based on gene prediction algorithms and may be interrogating regions that are not actually transcribed in a particular sample, or may be interrogating mistaken genomic assemblies, and hence do not correspond to biological reality. Such probesets will typically have low probe intensities corresponding to noise and the exon signal ill not generally track the gene signal. When the gene and probeset do correspond to biological reality, the gene may be poorly expressed or unexpressed in the biological samples. Both the gene and the probe set will have low probe intensities corresponding to noise and the ratio of exon signal to gene signal will have no meaning. Hence it is important that any statistical method based on the ratio of exon signal to gene signal should be able to handle low intensity probe sets.

Handling of probesets or genes not expressed in sample is an active area of research and while there is no specific assessment of the methods in the context of the model breakdown above, we took the following steps to guard against model breakdown:

Stabilize Variance

Most of the models discussed use the log ratio of exon signal to gene signal and for these we stabilized variance by adding a constant to the PLIER signal estimate before taking the ratio. This trades bias for variance. We chose a constant approximately equal to the 20%-ile of probeset signals. This appears to be well within the background level of probeset signals and since the core constitutive genes tend to be well-expressed, the bias will be relatively small.

Use Exon-Level Models

Probe sets that show only noise against a backdrop of true variation in gene signal will tend to generate higher values using MIDAS F-statistics. If the detection statistic is calculated for the gene as a whole, then such exons must be removed before this calculation otherwise the gene will be flagged as a candidate for alternative splice events. The robust nature of PLIER may be exploited to obtain estimates of gene signal to automatically filter out such probesets from the gene signal; this favors an exon-level approach.

Performance Evaluation

A ROC curve measures how well a statistic differentiates true alternatives from false positives. To do this exactly requires a known set that do not exhibit alternative splicing (the null set) to be compared with a known set that do exhibit alternative splicing (the alternative set). However, in our situation, we do not have complete knowledge, and hence the null set is likely contaminated by some real alternative splicing.

The effect of mixing some true alternative splice data into the null set will tend to cause the ROC curves to be constrained to a diamond (Bourgon, in preparation) around the diagonal of ROC plot and hence reduce the differences between statistics for large p-values. Mixing null data into the alternative set also affects the shape of the diamond; in this case the differences between statistics for small p-values will be affected.

It is expected that small p-values are more important than large p-values in assessing performance of different statistics that detect alternative splicing, and hence the error in construction of the null set is unimportant in our conclusion. In any case, qualitatively the empirical ROC curves are well-behaved; errors in construction of the null set probably do not affect p-values less than 0.1

Tissue Data Set Performance

Results vary considerably depending on the data set. With no filtering for the tissue panel both PAC and MIDAS perform equivalently.

Colon Cancer/Normal Data Set Performance

Figure 2:
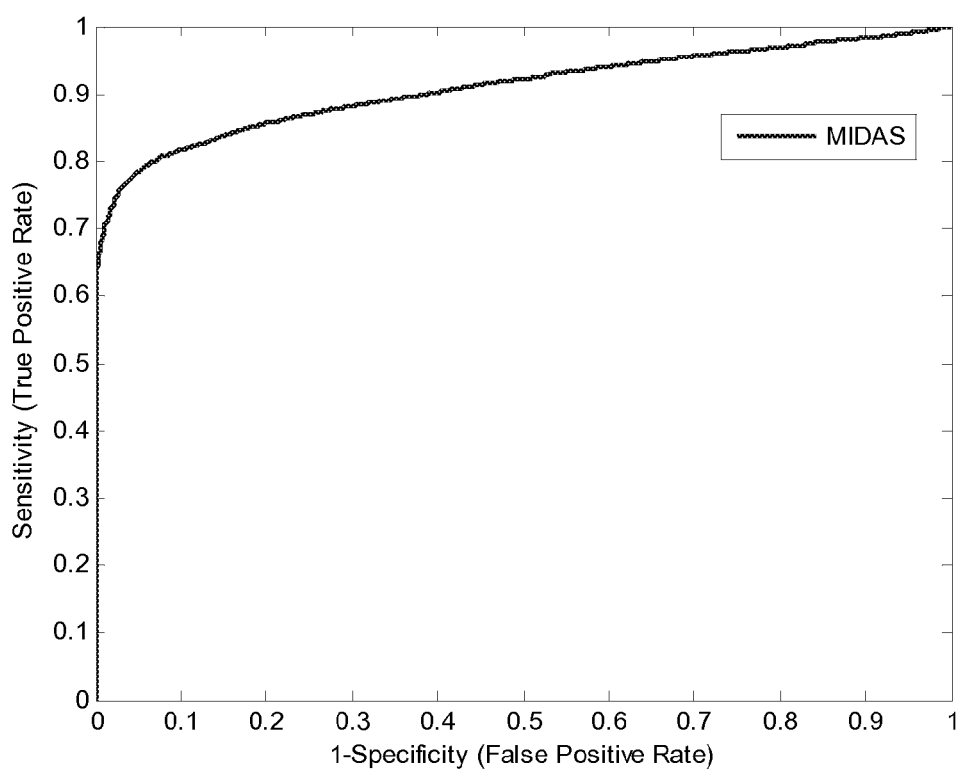
FIG. 2: ROC curve for Colon samples (Normal vs. Tumor) using MIDAS

On the colon cancer data set, PAC is not applicable, and MIDAS reduces to a 2-sample t-test. (See FIG. 2. ROC curve for Colon samples (Normal vs. Tumor) using MIDAS).

Methods Stratified by Number of Exons per Gene

Figure 3:
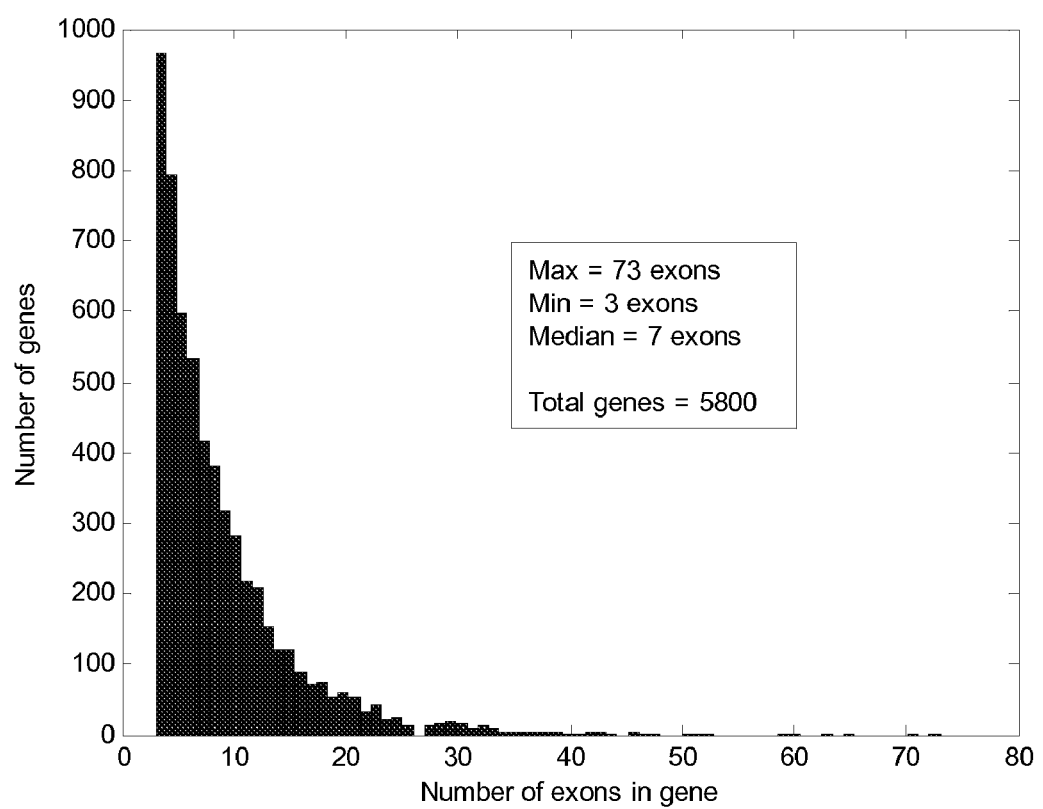
FIG. 3: Histogram of exons per Constitutive Core Gene

A histogram of the distribution of exons is shown below in FIG. 3:

We split exons into approximately 5 equal groups binned by number of exons per gene (Error! Reference source not found.):

| Min exons/gene | 3+ | 5+ | 10+ |
|---|---|---|---|
| Max exons/gene | 5 | 10 | 15 |
| Number genes | 1762 | 2252 | 1786 |

We see fairly similar ROC curves, with discrimination improving with larger number of exons per gene, possibly because the PLIER estimate of gene signal is more stable with a larger number of exons.

In practice, using exon-level detection instead of gene-level detection forces the issue of multiple comparisons, where the larger the number of exons in the gene, the greater the chance of high statistical significance by chance alone.

Figure 4:
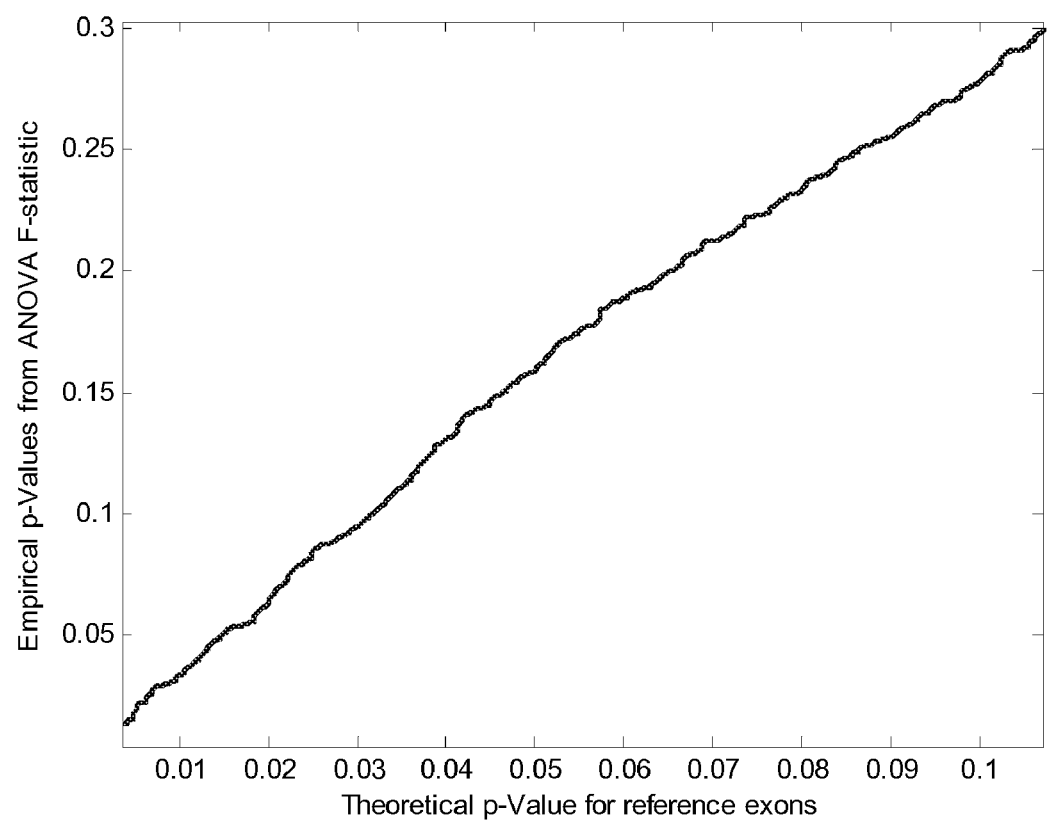
FIG. 4: Comparison of Empirical p-Values with Theoretical p-Values

In practice it is also desirable to use p-values. Using MIDAS on the tissue panel data, the ANOVA F-statistic gives p-values that are about 3 times too low (FIG. 4) Comparison of Empirical p-Values with Theoretical p-Values), so in practice one would not want to take p-values too seriously. Different structure in replicates and sampling might not give the same relation.

Using the method on RefSeq genes, highly significant p-values can be associated with exons and genes that consistently exhibit low expression across sample types (model failures as discussed below). P-values can also be high when an exon from one gene is incorrectly assigned to another gene. While the ratio of exon signal to gene is variable, observing a very high ratio in one or more of the sample types is an indication that an error of this type may have occurred.

Exon Array Background Correction: Similar performance is expected in detection of differential changes for most applications on exon arrays using the background probe collection (BGP) as opposed to specific mismatch probes (MM). (For example, the GeneChip® Human Exon 1.0 ST Array has a "genomic" and an "antigenomic" background probe collection. See below for more information on the background probe collections.)

The use of BGP probes to perform a PM-GCBG correction is described herein. PM-GCBG refers to the use of the median BGP intensity for BGP probes with the same GC content as the perfect match (PM) probe.

MM probes provide controls similar in sequence and location which are useful in removing bias; this takes one probe per informative probe. Because the MM probes hybridize to the perfect match (PM) target, when MM intensities are subtracted from PM intensities the PM response to true target slightly reduced. BGP probes provide a rough estimate of background based on coarsely modeled sequence, without taking into account any spatial variation. Use of BGP over MM probes requires roughly 50% less space on the array; thus use of BGP probes allows roughly a 2 fold increase in PM content.

Background estimates from BGP and MM probes may not be accurate for specific PM probes leading to biases in the background estimates results. We therefore look at the typical distribution of error in modeling background, as well as the downstream results on the ability to detect differential change. These results are based on a research array design using a pre-optimized version of the whole transcript assay.

We examine the performance of these two methods with a controlled experiment on a research chip using spiked-in transcripts. This experiment consists of 9 full-length clones which are spiked in at several different levels of relative abundance, with three replicates per level of abundance. The levels are arranged in a standard latin square design so that each experimental pool has some transcripts at each level of abundance, and every transcript occurs at all levels of abundance. In this experiment, the standard HeLa background is used as a complex background, and is not varied. This experiment was performed on an initial testing array design("WTA-Sensor" with a pre-optimized version of the whole transcript assay. protocol. This array design contained probes designed to complement every other base in the full-length transcripts. For analysis purposes, the transcripts were divided into twenty sub-regions each (simulating exons), and four probes were chosen to represent each sub-region, leading to twenty probe sets per transcript, or 180 probe sets analyzed in the data set used here.

Figure 5:
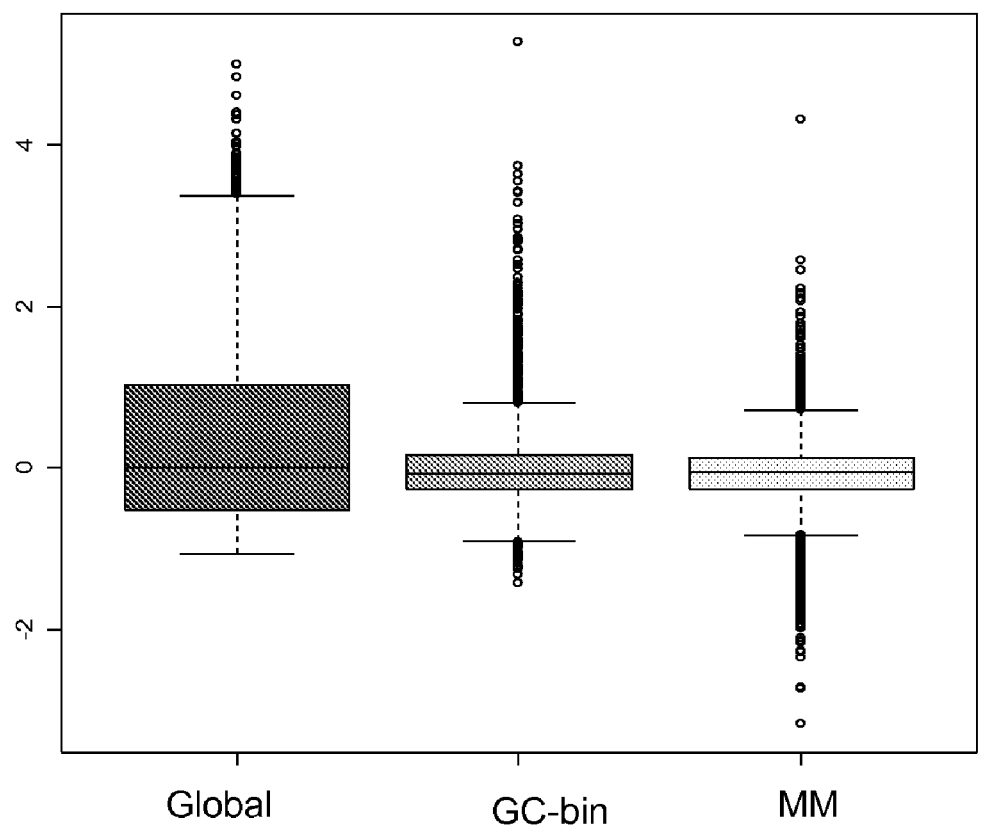
FIG. 5: The log-scale error in approximating background by three techniques: global, gc-bin averages using BGP, and individual mismatches (MM) is shown here for 8,103 GC-bin probes.

In FIG. 5, the distribution of multiplicative error for three different background models is displayed for a collection of background probes. By design, these should all be without specific hybridization, and hence an ideal background model would exactly predict the intensity of these probes. What is displayed in FIG. 5 is a boxplot of the residuals $\log(I)-\log(B)$ for each model. The first model is the log-scale error involved in approximating the background for probes of differing GC content by a single, universal background quantity, in this case, the median intensity. The second model sets the background estimate for a given probe to be the median of the corresponding bin of probes with similar GC-content, i.e $\log(I)-\log(B(GC))$. The last model sets the background estimate to be the corresponding MM probe. Both MM and GC-bin medians closely follow the behavior of probes across a wide range of GC-content, although GC-bin medians are slightly biased. Using a single global estimate of background has an unacceptably large distribution of errors in background prediction, however, GC-bin medians are sufficiently low error to be considered as replacements for specific MM probes.

Figure 6:
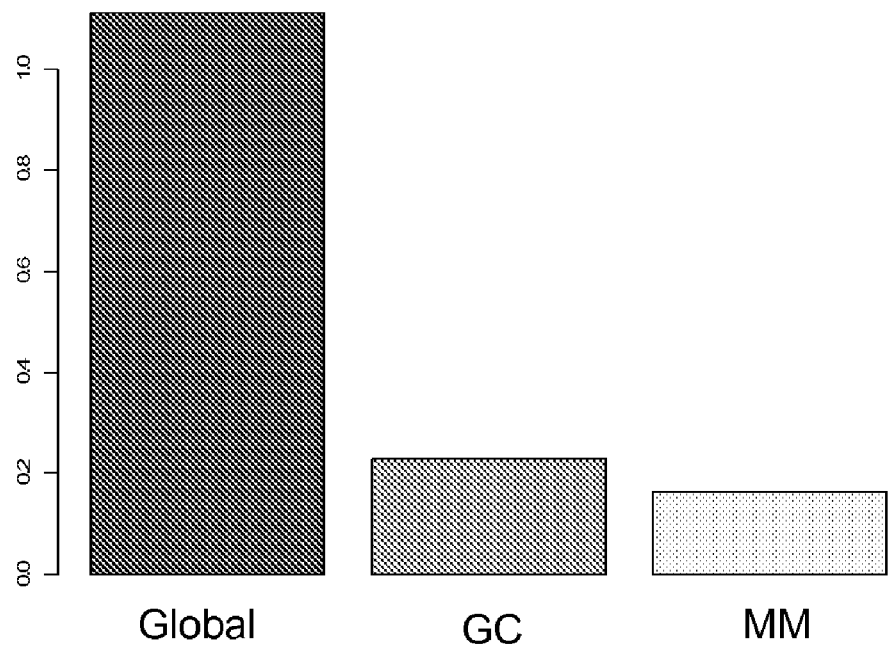
FIG. 6: Despite the similarity in the boxplots, mismatched probes (MM) are still a better approximation in mean-squared error (log-scale). However, since there is some loss of signal due to MM hybridization to the desired target, this extra variation does not greatly impact signal accuracy.
Figure 7:
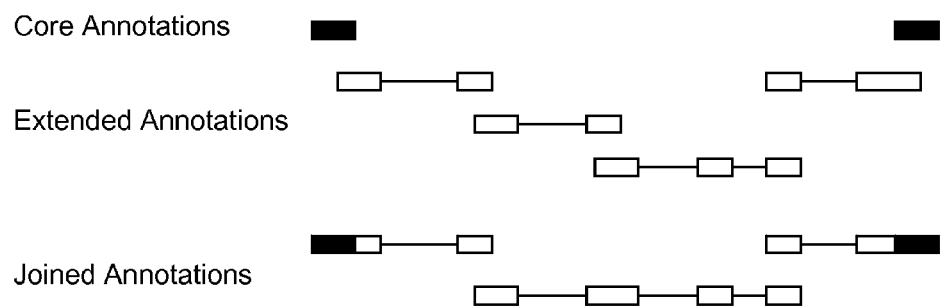
FIG. 7: (Rule 2e) Extended annotations that do not directly overlap any core annotations are not added to those associated clusters. Instead they are merged to form a cluster of their own.
Figure 8:
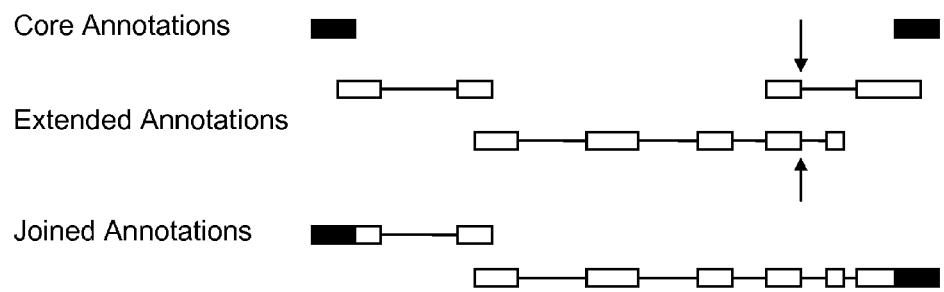
Figure 9:
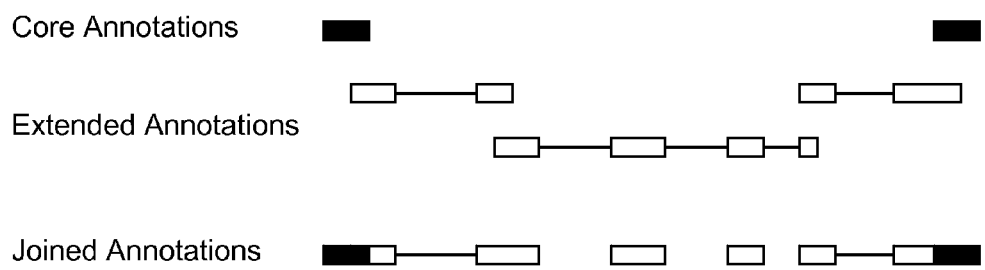
FIG. 9: (Rule 2c) The extended annotation is broken up into underlying exons because it overlaps two gene clusters from a higher confidence level.
Figure 10:
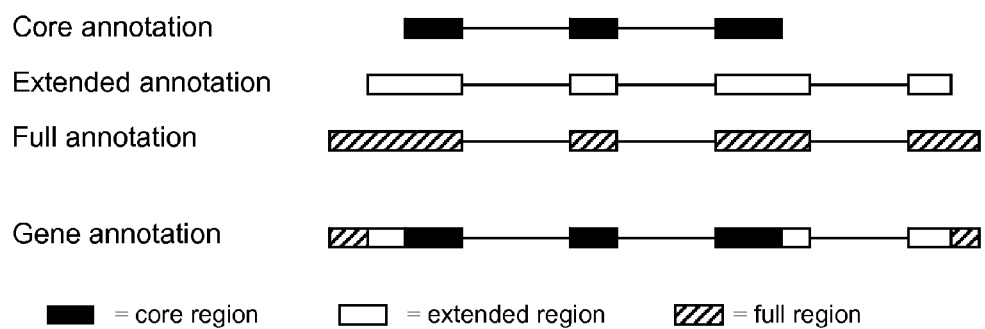
FIG. 10: Transcript annotations from different confidence levels are merged to form a gene annotation. The regions of the gene annotation can be labeled according to the highest level confidence transcript that supports that region.

FIG. 6 shows the mean-squared log-scale error resulting from each of the three considered models. Use of a single, global background estimate leads to large mean-square-error, and so is not acceptable for background estimation. Despite the very similar inter-quartile ranges for both the gc-bin background model residuals and the mm model residuals, the mean-square error is larger for gc-bin probes. However, the known tendency of mismatched probes to hybridize to the true target suggests that gc-bin background estimation may be sufficient for background estimation in the context of detecting differential changes in signal.

Using the same data set, performance was evaluated for the various background estimation methods. In this case, performance is measured by the ability to detect differential change between paired experiments. In the figure below we show receiver operator curves (ROCs) based on thresholding a t-like statistic between the different spike concentrations. Use of BGP over MM probes does not adversely affect the ability to detect differential change. It was observed however that some probesets exhibited more positive bias with BGP, indicating that coarsely modeled background with BGP does not completely remove bias from the data to the extent of the PM-MM method. It is important to note that these results are based on an assay that generates DNA target, not RNA target. Thus the observations for the whole transcript assay with regard to BGP may not hold for the 3' IVT assay.

Genomic and Antigenomic Background Probes

Genomic Background Probes: Background probes were selected from a research prototype human exon array design based on NCBI build 31. Mismatch probes were designed against Genscan Suboptimal exon predictions that were not supported by any other annotation source. When possible, 1000 mismatch probes were selected for each bin of GC content from 0 to 25.

Antigenomic Background Probes: The Antigenomic background probe sequences are derived from 15-mer root sequences that are not found in the human (NCBI build 34), mouse (NCBI build 32), or rat (HGSC build 3.1) genomes. These root sequences were extended by 5 bases on each end, where the added bases were drawn randomly from a GC distribution identical to the base 15-mer. There are probes for GC counts ranging from 2 to 24 per probe sequence. When possible, 1000 mismatch probes were selected for each bin of GC content.

Exon Probeset Annotations and Transcript Cluster Groupings

Procedures for grouping and annotating probesets are also disclosed. Appropriate grouping of probesets into transcript clusters and subsequent filtering of probesets within the transcript cluster plays a critical role in generating gene-level signal estimates. The annotations and groupings provided are intended to be a baseline of information for each exon array. How the information is applied will depend on the specific goals for each experiment. Definitions for terminology and array design are disclosed in the GeneChip Human Exon 1.0 ST Array Design Technote which is incorporated herein in its entirety for all purposes.

The GeneChip Human Exon 1.0 ST Array and other exon arrays are more exploratory than predecessor expression arrays such as the HG-U133 2.0 Plus. Previous array designs used a cDNA assembly consensus or exemplar approach where one or a few probeset were associated with a specific gene. For the exon arrays the design was exon focused rather than gene or transcript focused. As a result there are no intrinsic transcript or gene entities in the exon array designs. Instead there are only probesets associated with exons or contiguous parts of exons. Groupings of exon probesets into transcripts and genes is now a dynamic post-design process.

As new genome assemblies and annotations are released there is an opportunity to generated improved transcript cluster groupings. The meta-probeset lists available in the support files for the exon arrays are one such example of these groupings. Meta-probeset lists from different versions of the genome are likely to have different groupings of exon probesets into transcript cluster. Furthermore these different groupings may in turn have subtle (or even substantial) impacts on gene level analysis.

The basic approach used to generate transcript cluster groupings for a particular genome is to (1) construct gene annotations on the genome using a variety of annotation sources merged using a set of rules, (2) map exon probesets to gene annotations using the genome, and (3) use the target genome to group the probesets that mapped to the gene annotations. A fall out from this is that gene annotations are easily created from the transcript annotations used to group the probesets. The gene grouping process and probeset annotation process are described in more detail below.

The result of the entire process is a collection of "Design Annotation Files". These design annotation files are available from the appropriate exon array support page on the Affymetrix web site. Specifically, for each genome version a set of master GFF files are generated. These files are used to populate parts of the NetAffx content and are used to generate the other files including: design level probeset annotation CSV file, meta-probeset list files and IGB binary annotation (BGN) files Defining Gene Annotations The following five steps outline one method for grouping probesets. (1) Cluster transcript annotations on the same strand of the target genome using a set of rules involving exon overlap and splice site sharing. (2) Label each transcript cluster as a different gene. (3) Join exons of clustered transcript annotations on the target genome to determine gene structure. (4) Map each probeset to a single gene, based on whether it falls within the gene's annotated exon boundaries on the target genome. (5) Group probesets together that map to the same gene as a transcript cluster.

There are situations where simply clustering transcripts based on exon-exon overlap can produce gene annotations that actually represent multiple genes. Sometimes this is probably due to two genes actually sharing some transcribed region on the genome (i.e. 3' UTR of one gene overlapping the 5' UTR of a downstream gene on the same strand). In other cases this is due to erroneous cDNA sequences, alignment algorithms, or gene predictions. There was an effort to avoid such over-clustering of transcripts, even at the expense of fragmenting some gene annotations. This decision was motivated by the fact that falsely joined exons (from more than one gene) would generate results which at first pass would appear to be alternative splicing.

Gene annotations were constructed from clusters of transcript annotations. Because of the wide variety of transcript annotations sources, it was desirable to find a way to qualitatively categorize the different types of sources. For example, RefSeq sequences are manually curated and generally trusted as accurate isoforms of genes. While ESTs and partial mRNAs are not manually curated, they cover greater portions of the target genomes and are supported by the fact that they are derived from cloned sequence. And although ab-initio gene predictions are not inherently supported by clone sequence, they may be reasonable predictors of transcript structures. Acknowledging that different annotation sources have different levels of confidence, an iterative approach was implemented to ensure that high confident annotations were not merged by less confident annotations.

For the purposes of establishing a hierarchy of gene confidence levels, the sources of input transcript annotations were partitioned into three types. From highest to lowest confidence, the types were labeled core, extended, and full. Broadly defined, the core type consisted of (BLAT) alignments of mRNA with annotated full-length CDS regions, the extended type consisted of cDNA alignments and annotations based on cDNA alignments, and the full type consisted of sets of ab-initio gene predictions.

For the GeneChip Human Exon 1.0 ST Array, the annotation sources for each level are: Core Gene Annotation sources, RefSeq alignments, Genbank alignments of 'complete CDS' transcripts, Extended Gene Annotation sources, cDNA alignments, Ensembl annotations (Hubbard, T. et al.), Mapped syntenic mRNA from rat and mouse, microRNA annotations, Mitomap annotations, Vegagene (The HAVANA group, Hillier et al., Heilig et al.), VegaPseudogene (The HAVANA group, Hillier et al., Heilig et al.), Full Gene Annotations, Geneid (Grup de Recerca en Informática Biomédica), Genscan (Burge, C. et al.), GENSCAN Suboptimal (Burge, C. et al.), Exoniphy (Siepel et al.), RNAgene (Sean Eddy Lab), and SgpGene (Grup de Recerca en Informática Biomédica), TWINSCAN (Korf, I. et al.).

The core type was so named because the annotations in this type were intended to be the foundation from which we built our gene annotations. The extended type derived its name from the sense that these annotations would extend the boundaries of the core genes. The idea behind the name of the full type was that it would signify all possible content.

The transcript annotation clustering procedure utilized the confidence rankings of the transcripts in such a way that non-overlapping transcripts from a higher rank could not be joined together by a transcript annotation from a lower rank. For example, annotations of EST alignments would not be used as evidence to join two separate RefSeq alignment annotations—however, a third RefSeq alignment annotation could. Lower ranking annotations could only be added to the transcript clusters established at a higher ranking, or they would establish new clusters without any higher ranking content.

In one embodiment the algorithm for clustering the transcript annotations is as follows:

1) Core annotations are merged first.
   a. Spliced core annotations are merged first.
      i. If two core annotations share a splice site, they belong to the same cluster.
      ii. If two core annotations overlap with two different exons in each transcript, they belong to the same cluster.
      iii. If a core annotation lies within the boundaries of exactly one other core exon, the two belong to the same cluster.
   b. Single exon core annotations are added next.
      i. If a single exon core annotation overlaps an exon of exactly one spliced core cluster, it is added to that cluster. (However, the single exon is not used to determine exon overlap for subsequent single exon core annotations—i.e. prevent "chaining" single exons).
      ii. If a single exon core annotation lies within the boundaries of exactly one other core exon, the two belong to the same cluster.
      iii. Single exon core annotations that don't overlap any spliced core annotations are merged with each other based on overlap.
      iv. If a cluster of single exon core annotations formed in step (iii) overlaps with exactly one other spliced core cluster (with the single exons from step
         (i) now included), it is added to the spliced cluster (i.e. now allow chaining if it is completely unambiguous)
2) Extended annotations are added next, in a similar manner as the single exon core annotations.
   c. If an extended annotation exon overlaps the exon of exactly one core cluster or shares a splice site with exactly one core cluster, it is added to that cluster. (However, the added extended annotation is not used to determine exon overlap for subsequent extended annotations.)
   d. If an extended annotation falls entirely within the bounds of exactly one core exon, the extended annotation is added to that core cluster.
   e. If a spliced extended annotation overlaps the exons of more than one core cluster and does not share a splice site with exactly one of them, the extended annotation is broken up into its underlying exons. These underlying exons are then treated as separate single exon transcripts for the purposes of merging.
   f. Extended annotations that don't overlap any core clusters are merged with each other.

g. If a cluster of extended annotations formed in step (d) overlaps exactly one other core cluster (with the extended annotations from step (a) now included), it is added to that core cluster.
3) Full annotations are added last, in exactly the same manner as the extended annotations, except that extended clusters are treated the same way as core clusters.

FIGS. 7-10 illustrate hypothetical examples of how some of the rules for clustering transcript annotations may be applied.

The resulting transcript clusters define a set of exon boundaries, which in turn determine the gene definitions used for probeset clustering. Each gene annotation is constructed from transcript annotations from one or more confidence levels. Some parts of a gene annotation may derive from high confidence core annotations, while other parts derive from the lower confidence extended or full annotations. Therefore, different parts of the gene annotation can be labeled according to the highest confidence level of transcript annotation that supports that part. This labeling of the resulting gene annotations according to confidence level was used to further annotate the probesets that mapped to the gene.

Probeset Gene Mapping and Probeset Grouping

Probesets were grouped together if they mapped to the same gene annotation. Generally, a probeset was said to map to a gene annotation if it fell inside the exon of that gene. However there were cases that were not so straight-forward, and so a set of specific rules was established. (1) If a Probe Selection Region (PSR) overlaps exactly one gene, then the associated probeset is mapped to that gene (even if the probeset does not overlap any genes). (2) If a probeset falls entirely within the exon bounds of exactly one gene, then it is mapped to that gene. (3) If a probeset falls entirely within the exons of multiple genes, the probeset is mapped to its own unique transcript, unless the probeset falls within the exons of multiple genes, but within the core region of only one gene, then it is mapped to the gene with the core region (4) If a PSR or probeset does not overlap any genes, the probeset is mapped to its own unique transcript.

There were some cases where probesets were selected from Probe Selection Regions (PSRs) that were based on content that was removed after the design. Rule 1 attempted to associate the probesets from these PSRs with the genes that they were proximal to.

Cases where probesets fell within exons from multiple genes were covered by Rule 3, however there were special cases involving core genes. If a probeset fell within the exons of multiple genes, but only one of them was a core gene, then the probeset was mapped to the core gene. The motivation behind this rule was that since core genes were regarded with the highest confidence, a probeset that fell within core exon should be mapped to that gene, despite the lower confidence content.

There were three types of annotation that were applied after the probesets had been grouped: (1) a confidence ranking, (2) whether the probeset was 'bounded' to a transcript cluster (less confident association) or actually contained (high confident association) and (3) whether the probeset was within a high quality CDS region. While all probesets were given a confidence ranking, the 'bounded' and 'CDS' flags were applied to only some probesets.

Figure 11:
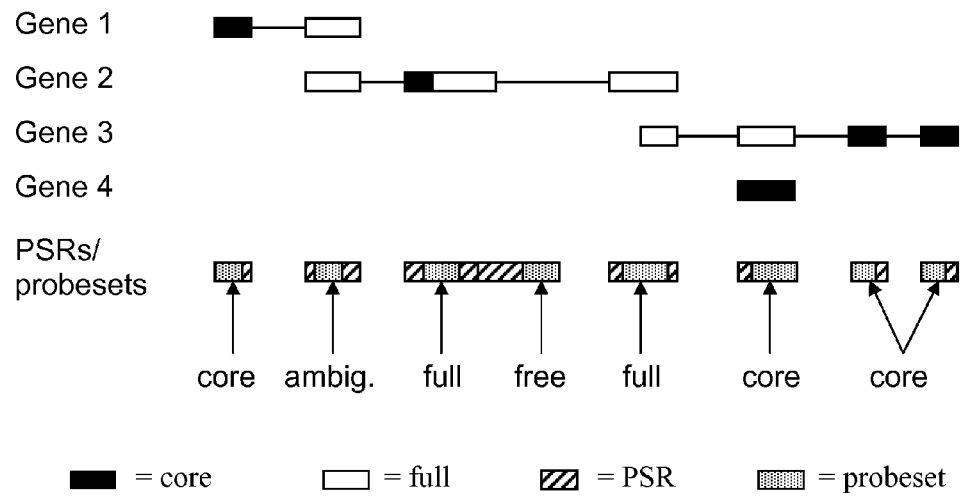
FIG. 11: Probesets are labeled with a confidence ranking according to the confidence level region of the overlapping gene. Probesets that fall within multiple genes are labeled 'ambiguous', unless the probeset falls within exactly one core region of a gene; then it is labeled 'core'. Probesets that overlap confidence region boundaries are labeled with the lower confidence level. Probesets that do not fall within any genes are labeled 'free'.

The annotations used to generate the gene bound definitions were further used to rank the probesets with respect to their confidence level. As mentioned above, the gene annotations used to group the probesets had core, extended, or full regions according to the confidence level of the transcript annotations used to compose the gene. A probeset with a position in the gene that was within a core region of the gene was given a 'core' level ranking. Likewise for probesets that fell within the extended and full regions of their associated genes. In the cases where a probeset crossed level boundaries, the probeset was labeled with the lower confidence rating. If a probeset did not overlap any genes, it was labeled as 'free'. See FIG. 11.

There were other instances where a probeset fit inside the exon of more than one gene annotation, and no determination could be made as to which gene annotation it belonged to. In these cases, these probeset was labeled 'ambiguous' and placed singly in its own gene annotation. The exception to this rule was if a probeset mapped to the exons of multiple genes, but fell within the core region of only one gene. Then the probeset was given the core level annotation instead of 'ambiguous'.

Many of the genes generated by the transcript clustering procedure were actually single exon genes defined by either a solo GENSCAN Suboptimal exon annotation or a single exon EST alignment. These annotations occurred at relatively high frequency throughout the greater transcribed regions of the target genome. Many of these annotations occurred within the introns of larger, spliced, higher confidence genes. It was decided to include these probesets with the transcript clusters they fall in, but to provide annotations to the effect that the grouping confidence is lower. For example, this allows researchers to easily include or exclude these single exon probesets for alternative transcript analysis with the same locus.

Figure 12:
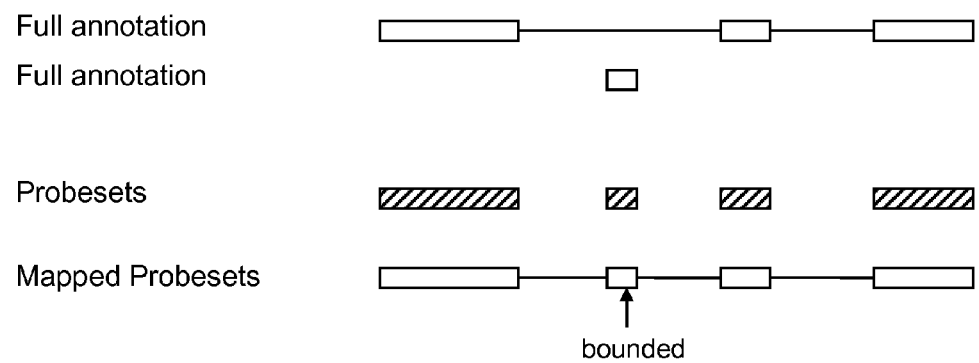
FIG. 12: Probesets mapping to non-core single exon annotations that fall within the intron of one other gene are grouped with that gene and given the label 'bounded'.

Therefore, if a probeset mapped to a single exon extended or full gene that lay within the intron of exactly one other gene, then the probeset would be "regrouped" as part of the larger, spliced gene and given the additional label, 'bounded'. The intuition behind the word 'bounded' is that the probeset is bounded by the larger spliced gene. See FIG. 12.

Probesets that fell completely within the CDS region of at least one transcript from one of the following four sources were flagged as 'cds' probesets: RefSeq alignments, Genbank alignments 'complete CDS' transcripts, Ensembl annotations, and VegaGene annotations. This allows research to quickly focus down to a set of probesets against likely protein coding regions.

Figure 13:
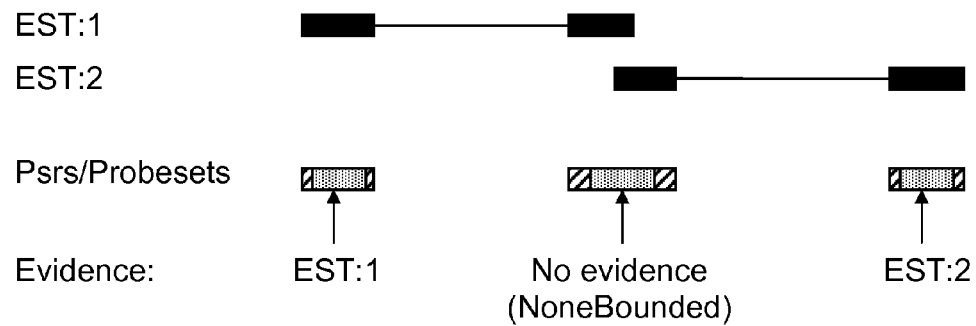
FIG. 13: An annotation is evidence for a probeset if the probeset lies completely within one of the exons of the annotation.

The probesets were further characterized by listing the quantity and source of annotations that could be interrogated by the probeset. The same transcript annotations used as building blocks for gene definitions were also used to describe the evidence for the probesets (although, in general any annotation set can be used here). As with the other labeling procedures, the entire probeset had to be bounded by the exons of the annotation in order for it to be listed as evidence. This technique for listing evidence gave rise to some non-intuitive situations where a probeset could have been given a confidence level of 'core', 'extended' or 'full', but not have any evidence. This is due to the fact that the transcript annotations were merged into larger gene annotations when determining the confidence levels, but were not merged when determining evidence for the probesets. Therefore, a probeset could be mapped to an exon that was derived from a composition of several smaller annotations, yet the probeset did not fall within the bounds of any one of these smaller annotations. See FIG. 13.

The mapping of exon array probesets to specific annotations is contained within the GFF file as comments. These GFF comments can be easily parsed should this level of information be needed.

These probeset groupings and annotations are meant to provide a starting point for researchers and are not intended as the final word on how probesets should be clustered and analyzed. While the notion of transcript clusters loosely equals a gene, it should be noted that we make no attempt to merge non-overlapping transcript clusters for the same gene (based on paired EST reads for instance).

Gene Signal Estimates from Exon Arrays

With exon arrays like the GeneChip® Human Exon 1.0 ST Array, researchers can examine the transcriptional profile of an entire gene. Being able to gather data for each individual exon enables the investigation of phenomena such as alternative splicing, alternative promoter usage, and alternative termination while also providing more probe level data to determine the overall rate of expression a particular locus. The calculation of a gene level signal estimate is of particular interest for many analysis as it provides a familiar starting point for the analysis of expression data. Generating gene level signal estimates from exon array data is the focus of this whitepaper. Throughout the rest of this article, the phrase "transcriptional locus", or "locus", will describe a genome location that is transcribed rather than using the term "gene" which often implies protein-coding transcripts.

The GeneChip® Human Exon 1.0 ST Array is inclusive by design. In addition to containing probe sets that interrogate exons of RefSeq (Pruitt and Maglott, *Nucleic Acids Res* 29: 137-140, 2001) genes, mRNAs and ESTs from GenBank (Benson et al. GenBank. *Nucleic Acids Res* 27: 12-171999), it also contains probe sets for exons predicted by ab-initio gene finders such as GENSCAN (Burge and Karlin J *Mol Biol* 268: 78-94, 1997), TWINSCAN (Korf et al. *Bioinformatics* 17 Suppl 1: S140-148, 2001), geneid (Parra et al. *Genome Res* 10: 511-515, 2000), and even GENSCAN Suboptimal exon predictions. Having so much content on the array allows the detection of novel alternative events, but presents a new challenge. This is because including alternative exons can negatively affect the estimate for the entire transcriptional unit. Additionally, much of the content is exploratory in nature, such as the GENSCAN suboptimal predictions, and by nature will have a lower probability of being actually transcribed compared with other well-annotated sequences. Having such a rich set of possible probe sets for each locus provides both the benefit of more data and the challenge of finding the best probe sets to use for gene-level signal estimation in a given experimental study.

The first step in estimates signal for a particular locus is to determine the boundaries for each locus, or gene, and which probe sets are contained within the boundaries. It is important to avoid mistakenly joining two loci, or genes, that are transcribed separately or splitting a single locus in two or more loci. Affymetrix has used genomic annotations such as RefSeq, cDNAs, and gene predictions to create discrete locus definitions (Wheeler, Gene Bounds: Probe Set Grouping, Annotation, and Evidence. In *Affymetix White Papers.*2005). Briefly, annotations that overlap exons on the same genomic strand were iteratively merged into a larger locus annotation. The probe sets on the GeneChip Exon Array were then assigned to these locus annotations, thus partitioning them into distinct transcriptional units, corresponding in many cases to genes.

Different, sometimes nested, loci definitions were created for different levels of annotation confidence so that research can clearly identify more exploratory content from well annotated content. High confidence annotations such as RefSeq transcripts and full-length mRNAs make up the "core" loci. The core annotations in addition with all other cDNA based annotations make up the "extended" loci. The "full" loci are the extended loci plus the ab-initio gene predictions. There are many single exon annotations that do not overlap the exons of other multi-exon annotations, but are contained in the intron of a larger multi-exon annotation. In some cases, such as a suspected alternative exon, it may be desirable to associate these single exon annotations with the locus they are nested within. This is referred to as being "bounded" by an annotation.

Users may select what confidence level of loci definitions to use and also exclude probe sets associated with a particular annotation. For example, the exploratory GENSCAN Suboptimal probe sets will not be appropriate for studies examining transcription changes in well-annotated genes.

To explore the effect of uncertainty of which probe sets to use for estimating the signal of a particular locus using PLIER (Hubbell, Plier White Paper. In *Affymetix White Paper.*, 2005) signal estimates, the following experiments wereerformed:

Addition of decoy probe sets likely to have low signal to simulate the inclusion of speculative content that is rarely, if ever, transcribed.

Addition of decoy probe sets likely to have high signals that do not correlate with the original locus to simulate the effect of mistakenly adding probe sets from a transcriptionally distinct locus.

Effect of using probe sets from more speculative annotations.

Effect of adding probe sets likely to have low signals on the signal estimates of spike-in data sets.

Figure 14:
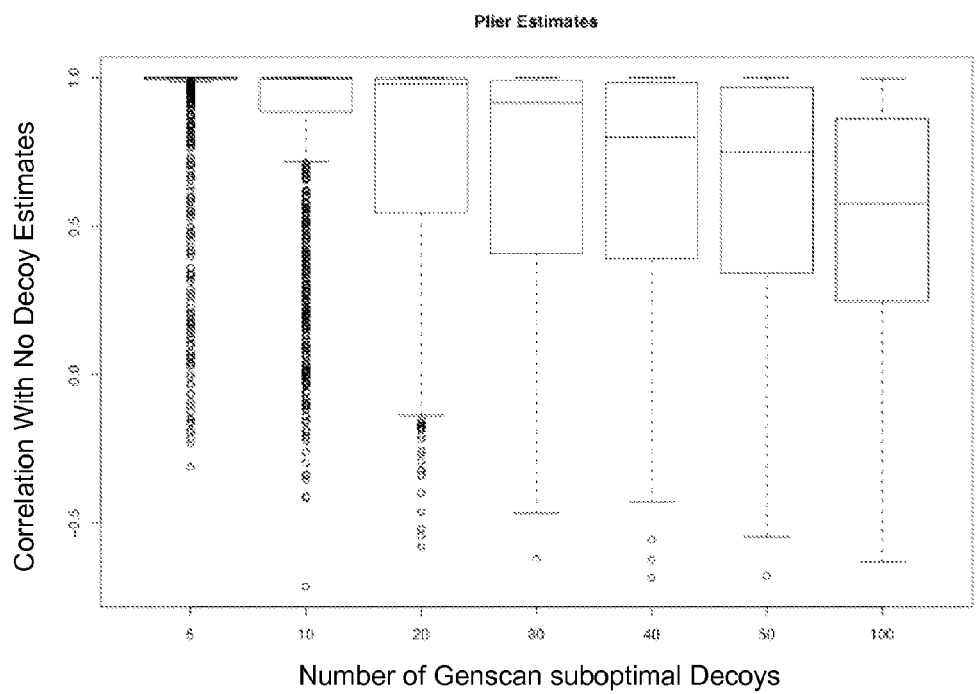
FIG. 14: Correlation with original estimates as low-signal decoy probe sets were added. As more low-signal GENSCAN Suboptimal decoy probe sets were added to the gold standard probe sets, the correlation with the original estimates decreases. However, the robustness of PLIER is evident as even when adding 10 unrelated probesets the correlation remains high.

Addition of Decoy Probe Sets:

Rather than generating simulated data we will sample from the GENSCAN suboptimal only probe sets as a proxy for low signal probe sets (mean PLIER estimated signal across all GeneChip arrays: 76+/−574) and the full length mRNA probe sets for high signal probe sets (mean PLIER estimated signal across all GeneChip arrays: 339+/−2,654). To facilitate the study of adding low- and high-signal decoy probe sets, we identified a set of probe sets that appeared to be constitutive for 1674 loci, with 4-11 constitutive probe sets in each locus, on chromosomes 1, 10, 11, 12, and 22. These constitutive probe sets were used as a gold standard to generate PLIER signal estimates for those loci. For this experiment, we used a set 48 GeneChip® Human Exon 1.0 ST Arrays hybridized to 16 different tissues with 3 technical (assay) replicates for each tissue. Tissue replicates were quantile normalized and then the different tissues were median normalized to each other. For both the low- and high-signal decoy probe sets, we then generated pair wise correlations for each PLIER estimate of the test case vs the PLIER estimate for the gold standard set (FIGS. 14 and 15).

Figure 15:
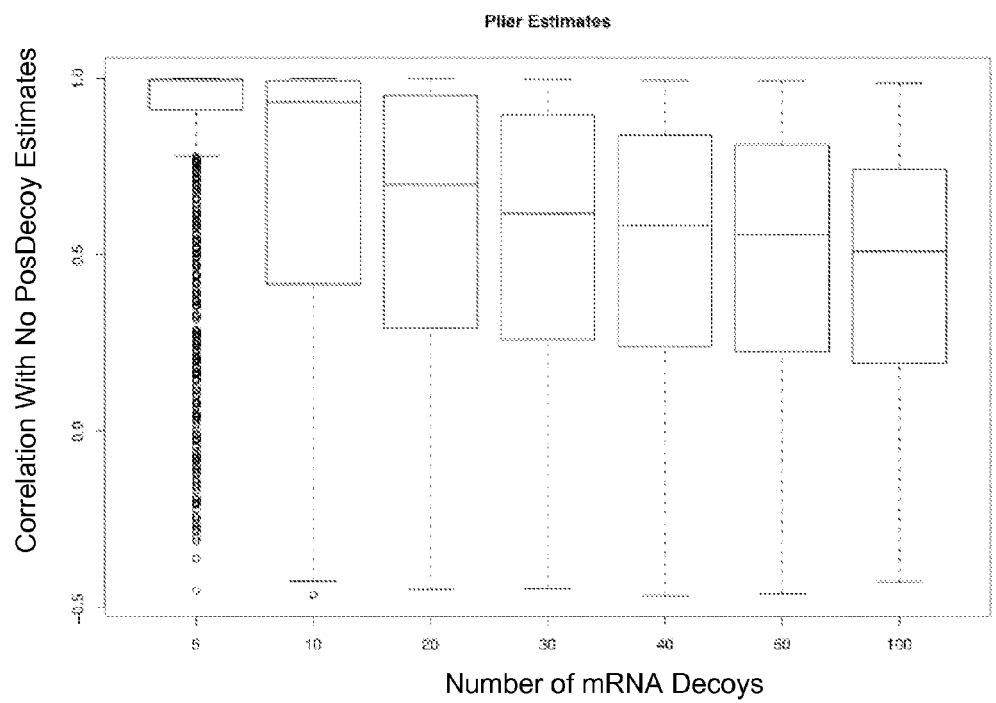
FIG. 15: Correlation with original Plier estimates as high-signal decoy probe sets were added. Including decoy probe sets from full length mRNAs decreases the correlation with the original estimates. PLIER is not as resistant to higher-signal decoy probe sets as it is to low-signal decoy probe sets (FIG. 16).

PLIER appeared relatively robust to the addition of limited amounts of low-signal decoy probe sets (FIG. 14), but was more affected by the addition of higher-signal decoy probe sets (FIG. 15). It should be noted that the addition of low-signal decoy probe sets will also reduce the absolute values of the PLIER estimates. As feature response of probes is constrained to have an average of 1, the low-signal probe sets make the other probe sets look like they are more sensitive to the presence of the target in comparison and thus reduce the signal estimate (see Hubbell 2005 for discussion of constraints)

Using More Speculative Annotations:

In addition to adding artificial decoy sets to the gold standard set described above, we also observed the effect of adding probe sets resulting from annotations that are more exploratory in nature for a particular locus. As probe sets with more speculative annotations are included in the loci expression estimates, the correlation with a bioinformatically enriched constitutive set becomes worse. The annotation file provided with Human Exon array details the annotations associated with each probe set. Using just the probe sets resulting from full-length mRNA and RefSeq exons results in loci expression estimates that are very highly correlated.

Expression estimates from extended annotations, those resulting from any cDNA, are also highly correlated with the gold standard set. Expression estimates from full annotations, those resulting from a gene prediction program, were also highly correlated, but not as much as the cDNA based annotations.

Including probe sets that were bounded by a gene (located in an intron, but not overlapping an exon) resulted in the lowest rate of correlation. The effect on a particular gene can be seen in the form of both lower PLIER estimates and lower correlation with the constitutive set across 48 samples. As more exploratory probe sets are added to the transcriptional locus estimates, the overall correlation is still high, but the range of PLIER estimates becomes compressed.

Figure 16:
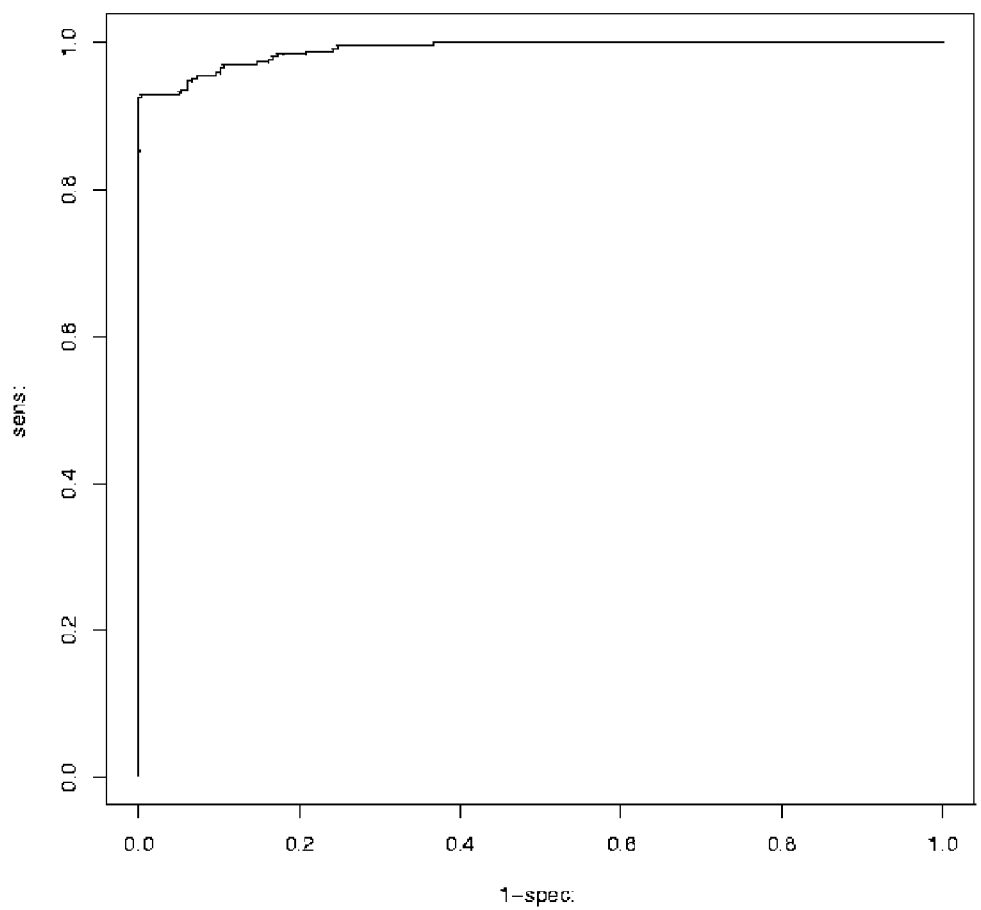
FIG. 16: Signal ROC Plot for Differentiating Between Spike-in Concentrations of 0.71 pM and 0.36 pM. With no decoy probe sets, the GeneChip Exon Array differentiates well between spike-ins at different concentrations and those added at the same concentration.
Figure 17:
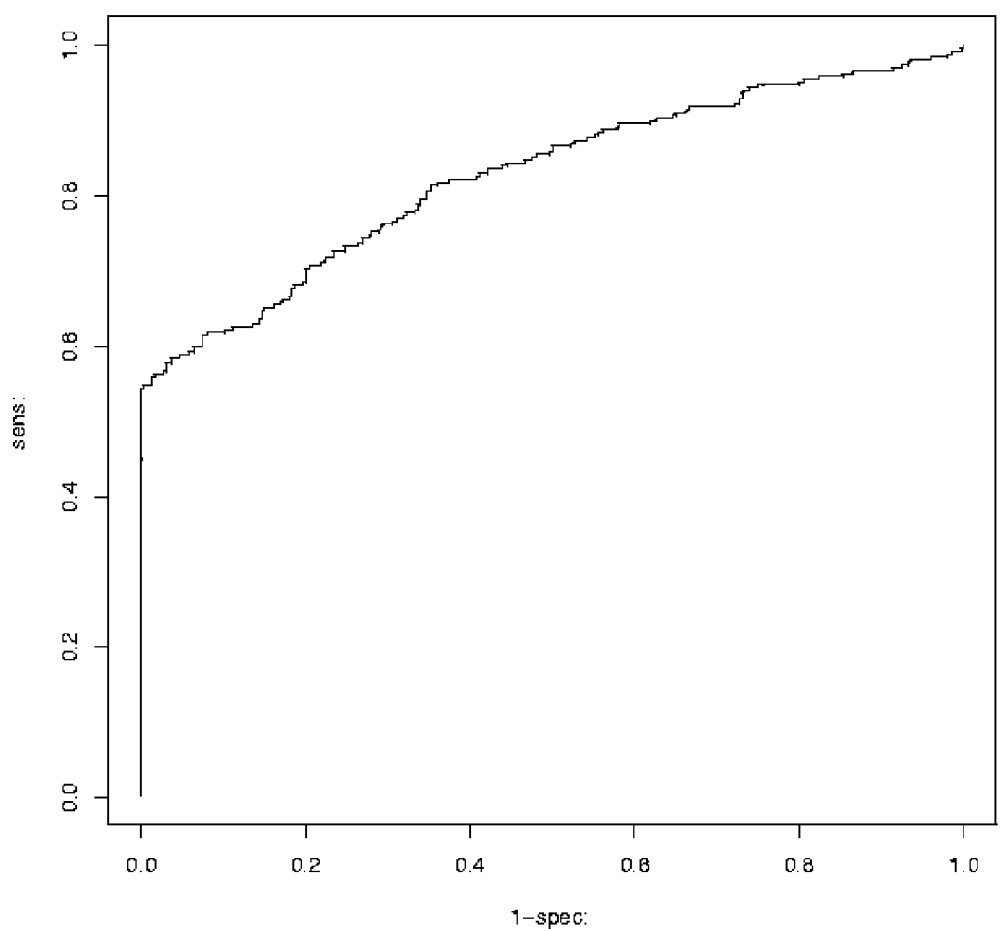
FIG. 17: Signal ROC Plot of Spike-in Concentration (0.71 pM vs 0.36 pM) Differentiation with 20 Decoy Probe Sets. The addition of low-signal probe sets decreases the ability of the PLIER expression estimates to differentiation between spike-in concentration pools.

Effect of Decoy Sets On Differentiating Known mRNA Concentrations:

We also investigated the effect of adding low-signal probe sets on the ability to differentiate between spiked-in concentrations of mRNAs. For this experiment, a latin square design was used with 4 groups of spike-in RNAs at 4 different concentrations of 0, 0.18, 0.36, and 0.71 pM with 3 replicates each. A receiver operator curve (ROC) was calculated with the ability to differentiate between spike-ins that are present in different concentrations and those present at the same concentrations (FIG. 16). The addition of low-signal decoy probe sets decreases the ability of the PLIER expression estimates to differentiate between spike-in concentration pools (FIG. 17).

Strategies for Coping with Exploratory Content:

One natural solution to determine which probe sets to use for summarizing a particular locus is to only use probe sets contained within high quality annotations such as RefSeq transcripts. Leveraging years of work cloning and sequencing genes combined with expert manual annotation assures that the probe sets chosen belong to that locus. This approach does not address the issue of including probe sets to alternative events, but if most exons are constitutive for a given gene, they should dominate the PLIER expression estimate rather than the alternative probe sets. Robust methods such as PLIER and RMA (Irizarry et al. *Nucleic Acids Res* 31: e15, 2003) should be minimally affected by a limited amount of alternative splicing at a particular locus.

Selecting Features to Use in a Given Data Set:

Another strategy is to use feature sets from more exploratory annotations and iteratively discard those that appear to be performing poorly. This approach takes advantage of PLIER's ability to identify some of the signal at a particular locus and iteratively exclude features that are not correlated with that signal. As a proof-of-principle study, we implemented a procedure, IterPLIER, to use all features to generate an initial PLIER estimate and found the 22 features best correlated with that estimate, re-estimated the expression estimate with those 22 features using PLIER and then selected 11 features that were best correlated with the new expression estimates to generate a final PLIER signal estimate.

Figure 18:
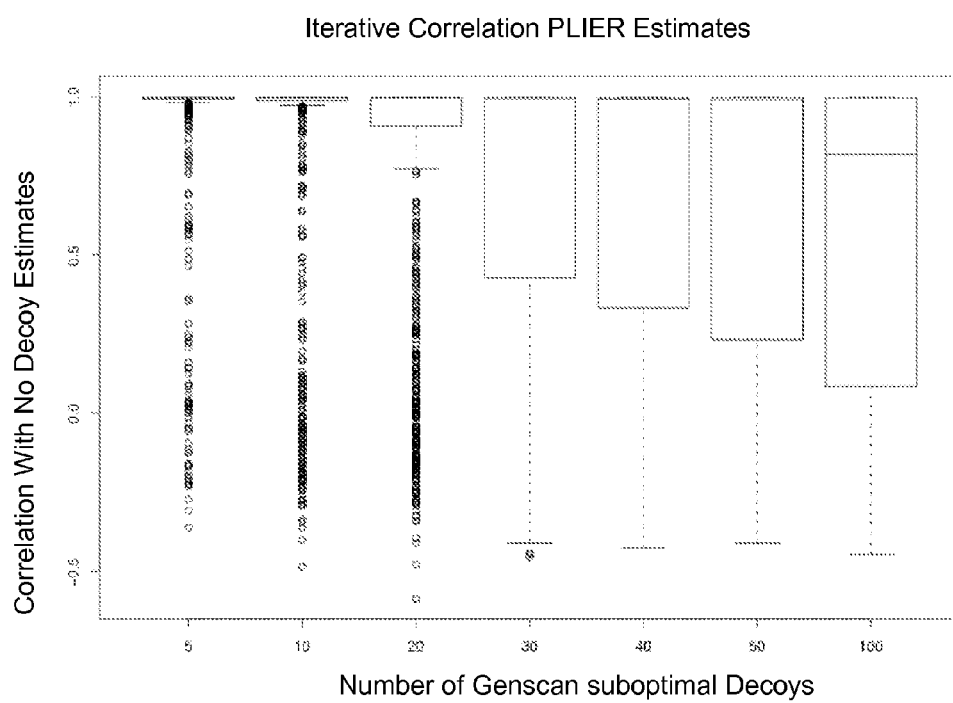
FIG. 18: Correlation with original set as low-intensity decoys are added using an IterPLIER. The IterPLIER expression estimates are better correlated to the gold standard PLIER expression estimates than the raw PLIER expression estimates.
Figure 19:
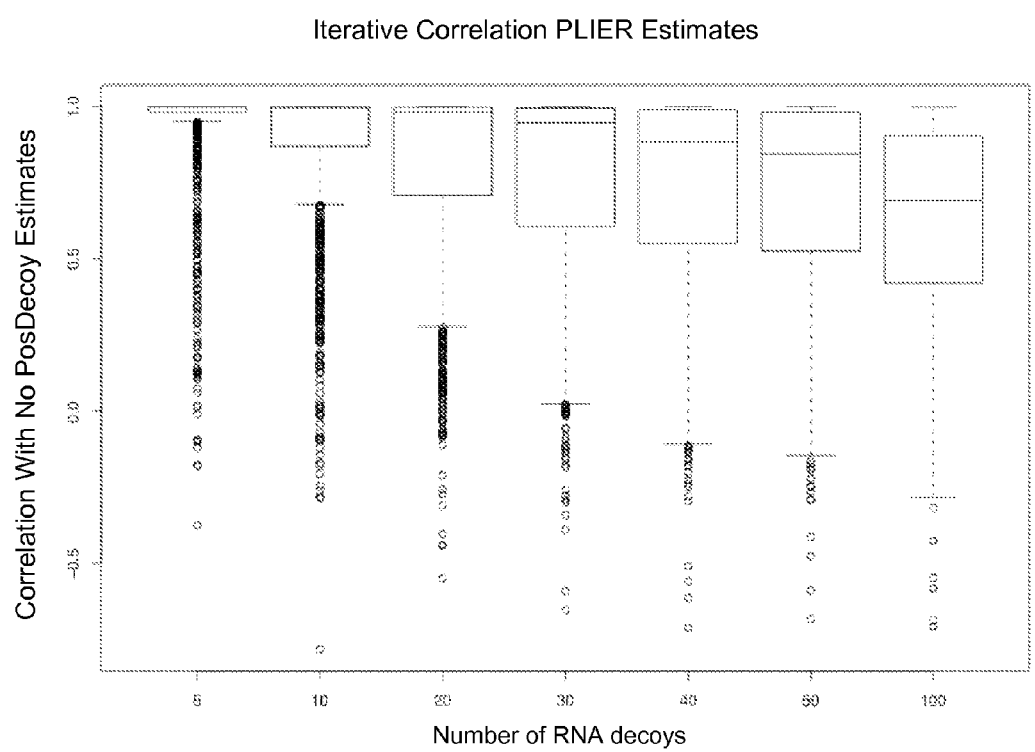
FIG. 19: Correlation with original set as high-intensity decoys are added using IterPLIER. The IterPLIER expression estimates are better correlated to the gold standard PLIER expression estimates than the raw PLIER expression estimates.
Figure 20:
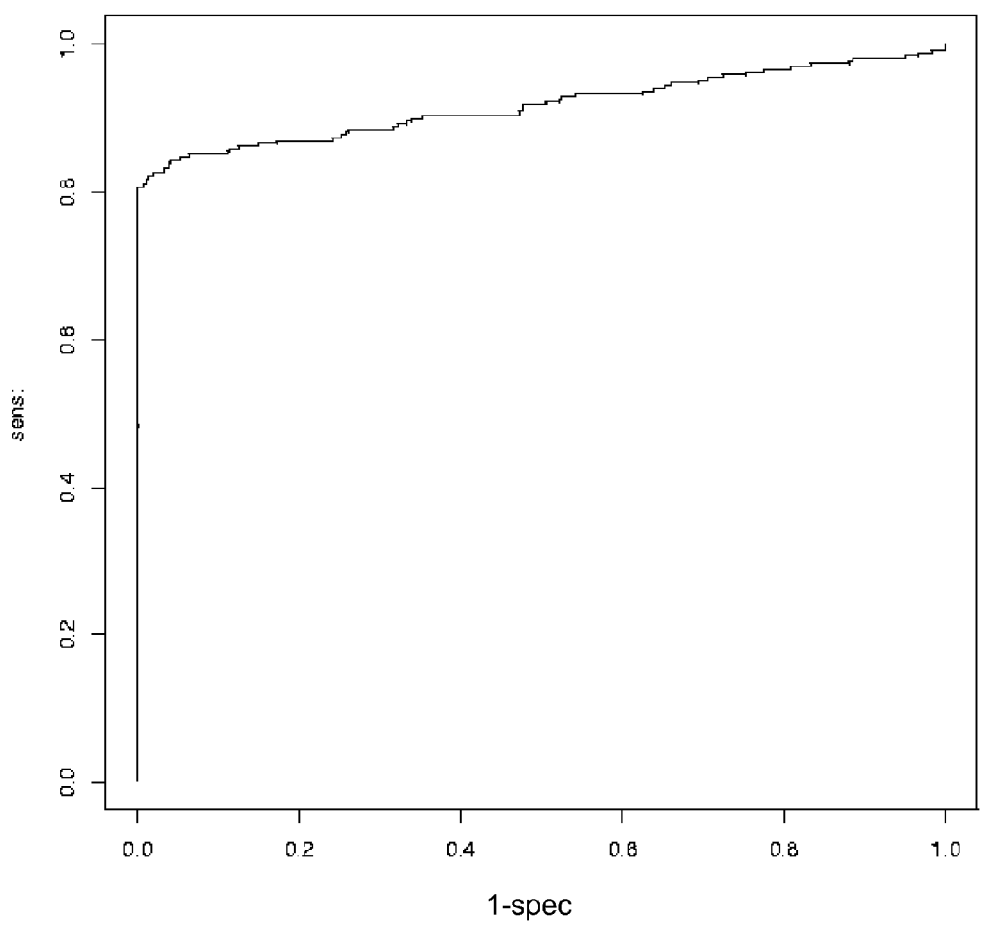
FIG. 20: IterPLIER Improves Signal ROC performance in Presence of 20 Decoy Probe Sets (0.71 pM vs 0.36 pM). The ability of IterPLIER expression estimates to differentiate between spike-in concentrations is improved compared to raw PLIER expression estimates.

The correlation with the signal estimates without decoy probe sets compared to the result of IterPLIER on the low-intensity decoy set (FIG. 18) and high-intensity decoy set (FIG. 19) are improved to those resulting from using the initial PLIER estimates. The results for IterPLIER on the Akt3 locus illustrate that signal estimates consistent with the original bioinformatically enriched constitutive gold standard set were obtained for all cases but the full-bounded set. These results compare favorably to the raw PLIER expression estimates. This illustrates the improved correlation for all but the full-bounded probe set groups. This method also improves the ability of PLIER expression estimates to differentiate between spike-in concentration pools in the latin square experiments. See FIG. 20.

Determining the best way to estimate locus intensity, and hence the underlying relative target response, is still an area of active research. Here we have shown that PLIER is more robust with respect to additional low-signal probe sets than to additional conflicting high-intensity probe sets. These results suggest that loci which may be transcribed separately should be joined with caution, while low confidence annotations may be included in an analysis with less risk. As the new Human Exon array has more data for each locus we now have an opportunity to improve our estimates, but also face more choices about the type of estimates that are most appropriate for the study at hand.

Quality Assessment of Exon Arrays

Quality assessment can play an important role at many stages in the process of generating gene expression data for biological samples, from array design to sample processing to signal estimation and analysis. In this report we describe some quality assessment procedures that are based on CEL intensity data from the GeneChip® Human Exon 1.0 ST Array. The methods detailed here are described in Chapter 3 of the Bioconductor monograph [Robert Gentleman, Vince Carey, Wolfgang Huber, Rafael Irizarry, Sandrine Dudoit, *Bioinformatics and Computational Biology Solutions using R and Bioconductor,* 2005.]. The quality assessment procedures we consider entail computing some summary statistics for each array in a comparable set and comparing the level of the summary statistics across the arrays. We therefore assume that the user has a set of comparable arrays of the sort that would normally be analyzed together to address substantive biological questions. The quality assessment part of the procedure entails identifying outliers within the set. These could be flagged and excluded from the substantive biological analysis, or the downstream analysis could be adjusted to account of the outlier arrays, by weighting for example.

The procedures we describe can identify outliers, but it does not provide hard and fast rules (specific thresholds) as to which arrays to flag as outliers. These need to be developed in the context of particular applications with specific types of samples, with knowledge of the costs involved in repeating experiments and the costs of drawing wrong conclusions. The procedures also do not provide guidelines to assess the overall quality of a set of arrays. These can be arrived at by collecting data for many sets of arrays and using them to set target levels and variance limits for the various quality assessment measures on a user-by-user basis. Lastly, while the methods presented here can be used to identify outlier arrays, they will not indicate why the array is an outlier (ie input RNA quality problem, target prep problem, hybridization problem, etc. . .)

The following are included below: simple summaries of the intensity distributions and $\log_2$ ratios of cel intensities, summaries of feature set model fit derivates—signal estimates and residuals, and the specific quality metrics reported in the Exon Array Computational Tool (EXACT) Quality Report.

Feature or cel level summaries. Note that the feature level graphs presented below are not directly obtainable from the Exon Array Computational Tool (ExACT). The "exact-probe-intensity-extraction" command line program can be used to extract probe level intensities for either the whole array or a subset of the features on the array. Normalized and un-normalized CEL files can be used with this tool. The extracted probe intensities can then be evaluated with a statistical application such as R, S-Plus, or MatLab to generate the summary graphs.

Single Array Cel Intensity Distribution Summaries

The simplest and most obvious thing to do with a set of cel files that have been collected for the purpose of addressing some questions of biological interest is to examine the distribution of cel intensities corresponding to each array in the set. As the array distribution of intensities is highly skewed, the $\log_2$ transformation helps to approximately normalize the distributions. Log base 2 is typically used as it facilitates the conversion back to the original scale: a difference of 1 on the log base 2 scale corresponds to a fold change of 2 on the original cel intensity scale. Array $\log_2$ cel intensity distributions can be summarized by a three point summary: $25^{th}$ percentile (Q1), $50^{th}$ percentile or median (Q2) and $75^{th}$ percentile (Q3). To identify outlier arrays within a set, it helps to compare the distribution by means of boxplots. In the boxplot display, a box is formed with sides at the $25^{th}$ and $75^{th}$ percentiles of the distribution. A line is also drawn within the box at the level of the median. Whiskers are also drawn extending beyond each end of the box with points beyond the whiskers typically indicating outliers. As the purpose of the boxplots in this application is to compare the location and spread of the main body of the distribution of $\log_2$ cel intensities, we typically suppress the plotting of symbols for points beyond the whiskers. See, Tukey, John W., *Exploratory Data Analysis*, Addison-Wesley, Reading, Mass., (1977) for guidelines regarding outlier detection.

Figure 21:
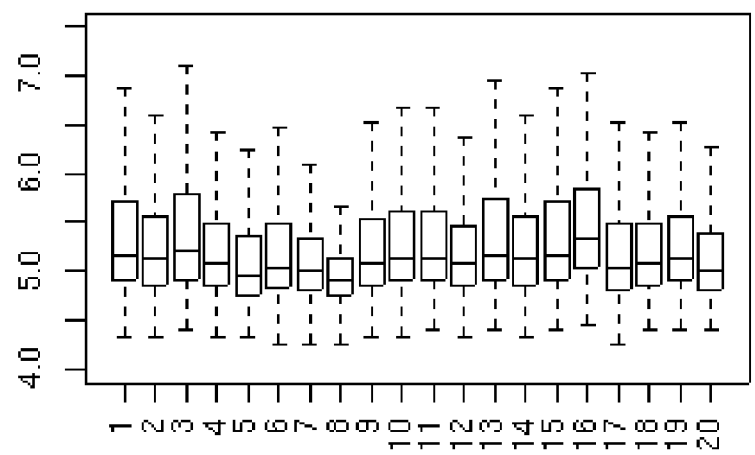
FIG. 21: Boxplots of log2 cell intensities for a set of 20 arrays.

FIG. 21 shows an example set of boxplots of $\log_2$ cel intensities for a set of 20 arrays. The 20 arrays were hybridized with preparations made from RNA extracted from colon tissue samples. We observe a range of cel intensity distributions across the 20 arrays. A normalization transformation is typically applied to make the distribution of cel intensities more comparable. Based on cel intensity distributions alone it is difficult to assess the impact that observed differences will have on downstream analysis. It is recommended that cel intensity distributions be observed and recorded for future reference.

Figure 22:
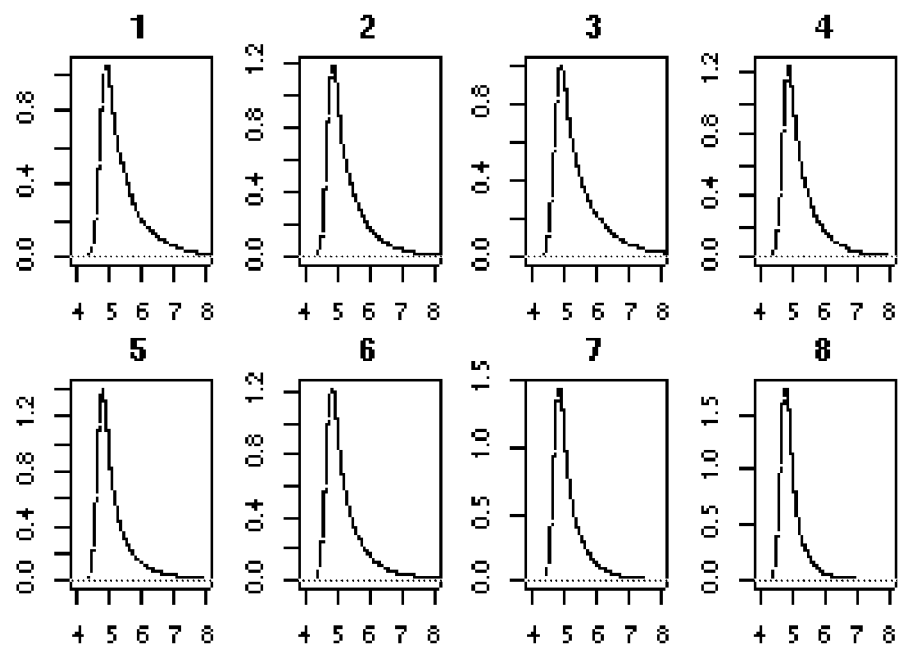
FIG. 22: Histograms of log2 cell intensities for the first 8 arrays in the set of 20.

$\log_2$ intensity distributions can also be summarized by means of a histogram display. Whereas histograms provide more detail, but makes the comparison of several distributions more difficult. Histograms enable the detection of a secondary mode in the distribution corresponding to a bright spot on the array. Unless the array images are examined to identify locally bright or dim regions, it may be warranted to examine the histograms of the $\log_2$ cel intensity distributions for any evidence of bright spots. FIG. 22 shows the histogram of $\log_2$ cel intensities for the first 8 arrays in the set of 20 displayed in FIG. 21. As there is no evidence of bi-modality, these displays provide no additional information to what is captured by the boxplots in FIG. 21.

Multiple Array Feature Level Summaries

A significant characteristic of CEL intensity data is the large magnitude of feature specific effects. The typical range of $\log_2$ CEL intensities for arrays in FIG. 21 is (lo, hi) (e.g. (2, 16)). The range of variability for any given feature, or CEL, across the set of arrays will be much lower—bright features tend to be bright across all arrays, and dim features tend to be dim across all arrays. The model used by PLIER (see PLIER Technote) to compute signal estimates, as well as the model used by RMA to compute feature set summaries, account for these feature effects. The MA-plot [Dudoit S, Yang Y H, Callow M J and Speed T P. *Statistical methods for identifying differentially expressed genes in replicated CDNA microarray experiements*. Statistica Sinica, 12:111-139,2002.] provides a visual display that corrects for feature-specific effects and facilitates making comparative assessments of cell intensity distributions that are sensitive to the technical variability which we want to detect. Suppose that x and y are two vectors of $\log_2$ intensities corresponding to two arrays. The MA-plot is a scatter plot of $M_i=(x_i-y_i)$ on the vertical axis vs. $A_i=(x_i+y_i)/2$ on the horizontal axis. The M values are relative $\log_2$ intensities, or $\log_2$ ratios of intensities. The median M value gives a sense of relative shift in $\log_2$ intensity between two arrays, and the inter-quartile range (Q3-Q1) of M values gives a sense of reproducibility of cell intensity values between arrays. The M values also contain some real biological variability, but for practical purposes that variability in M values provides a useful indicator to detect extra technical variability. The MA-plot as described above provides pair wise comparisons between any pair of arrays. When assessing quality in a set of arrays, pair wise comparisons produce much redundancy. To avoid this redundancy, each array can instead be compared to a synthetic array created by taking feature-wise medians across the set. For example application and interpretations of MA-plots see Dudoit et. al.

Figure 23:
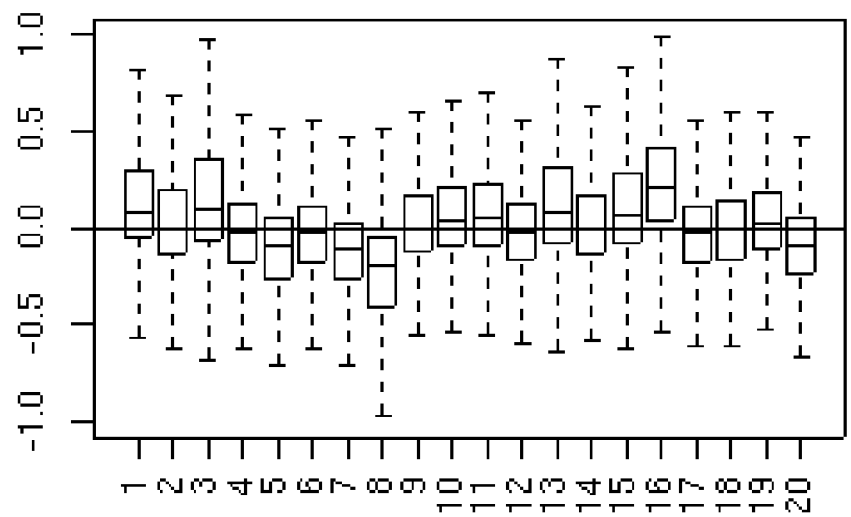
FIG. 23: Boxplots of M values for a set of arrays: M=relative log2 intensity=relative log2 intensity=log2 intensity for array—median log2 intensity

Boxplots of M values provide a summary of MA-plots which ignores the relationship between relative $\log_2$ intensity and mean $\log_2$ intensity but facilitates the comparative assessments of the distribution M values among many chips. FIG. 23 shows boxplots of relative $\log_2$ intensity values for the 20 arrays whose $\log_2$ intensity values are displayed in FIG. 21. The two FIGURES, FIG. 21 and FIG. 23, deliver the same message, with latter being more sensitive to differences between arrays. At this point, a word on normalization is in order. Ideally, the distributions of $\log_2$ cell intensities for a set of arrays to be analyzed together will be comparable—the three-point summary values (Q1, Q2, Q3) should be around the same level for all arrays, and the MA-plots should be flat, narrow and centered at zero. This ideal will rarely be achieved in practice due to the biological and technical variability that is an inherent characteristic of the cell intensity data being produced by a very elaborate process with multiple sources of variability. Normalization is the term used to refer to procedures that adjust cell intensity data in order to remove the technical variability without masking the biological variability. Some normalization methods will remove much of the variability that is detected by the quality assessment displays describe above. Assessing variability in the un-normalized data values is still important as the amount of adjustment that is required to normalize the cell intensities of an array is a good indicator of quality—the less adjustment required, the better the quality.

Summaries of feature set model derivatives. As mentioned above, feature-specific effects account for a large fraction of the variability in intensity between features. These feature effects are a function of sequence dependent probe affinities as well as the composition of the hybridization mixture hybed to the array. Models have been developed to account for feature effects by estimating these effects in a multi-array context. The models are typically fitted to a biologically meaningful set of arrays—RNA extracted from liver samples; samples characterized as normal or cancerous, for example. In this section we discuss quality assessments based on derivatives, or by-products, of the PLIER model fits. The models are fitted feature set by feature set and produce feature effect estimates, signal estimates and residuals. Feature effects are a nuisance parameter which yield improved signal estimates but can otherwise be ignored. Signal estimates are the expression indicators that will be used in the biological applications. They can also be used for quality assessment, as can the model residuals. The next two sections describe quality assessment measures that are based on these model-derived quantities. The analysis presented below can be performed in a variety of statistical analysis packages using the ExACT probeset summary output files as well as the option PLIER residual files.

Relative $\log_2$ signal summaries. After fitting the PLIER model to a set of arrays, we have signal estimates for each feature set and each array. We can assess data quality in terms of reproducibility of signal values across arrays as measured by $\log_2$ ratios of signal estimates or relative $\log_2$ signal. In a set of arrays hybridized to samples coming from distinct biological samples, some signal variability is expected due to real biological variability. Using a measure of variability based on the most reproducible relative $\log_2$ signal values—an inter-quartile range which in effect uses the 50% most reproducible signal values to assess reproducibility—produces a measure which can detect extra technical variability above and beyond biological variability. We can assess the reproducibility of signal estimates between two chips by means of an MA-plot, in which relative log signal is plotted on the vertical axis and average signal on the horizontal axis. As pair wise comparisons produce much redundancy, signal values for each array can instead be compared to signal values from a synthetic array constructed by computing for each feature set the median signal over all the arrays in the set. Superimposing the MA-plots with smooth curves capturing the quartiles (median, lower and upper quartiles) in relative $\log_2$ signal values as a function of average $\log_2$ signal is a helpful visual aid to detect subtle differences among MA-plots.

Figure 24:
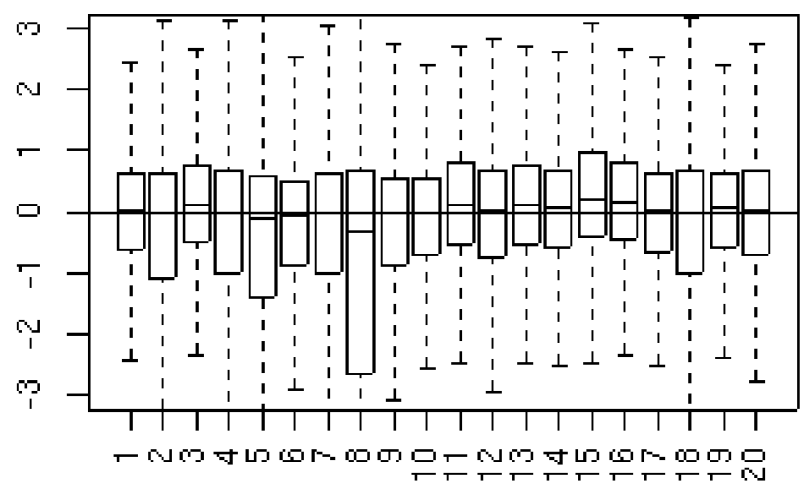
FIG. 24: Boxplots of M values for a set of arrays: M=relative log2 plier signal

Boxplots of relative $\log_2$ signal values provide a succinct summary of MA-plots which ignores the relationship between relative $\log_2$ signal and mean $\log_2$ signal but facilitates the comparative assessments of the distribution relative $\log_2$ signal values among many chips. FIG. 24 shows boxplots of relative log plier expression values for the set of arrays analyzed in FIG. 21. We see that with the except on of array number 8, at the plier signal level the arrays are comparable in expression level—the center of the boxplots close to zero—and reproducibility—the size of the boxplots are comparable. Based on these assessments, one would be advised to exclude the data from array 8 from downstream analyses.

In the assessment of reproducibility discussed so far we have implicitly assumed that the summaries would be computed based on all feature sets. We can generalize the above assessments by summarizing over a various collections of feature sets. One may wish, for example, to look at signal reproducibility in the normalizing exon feature sets, or the normalizing intron feature sets, or a random sample of feature sets.

Figure 25:
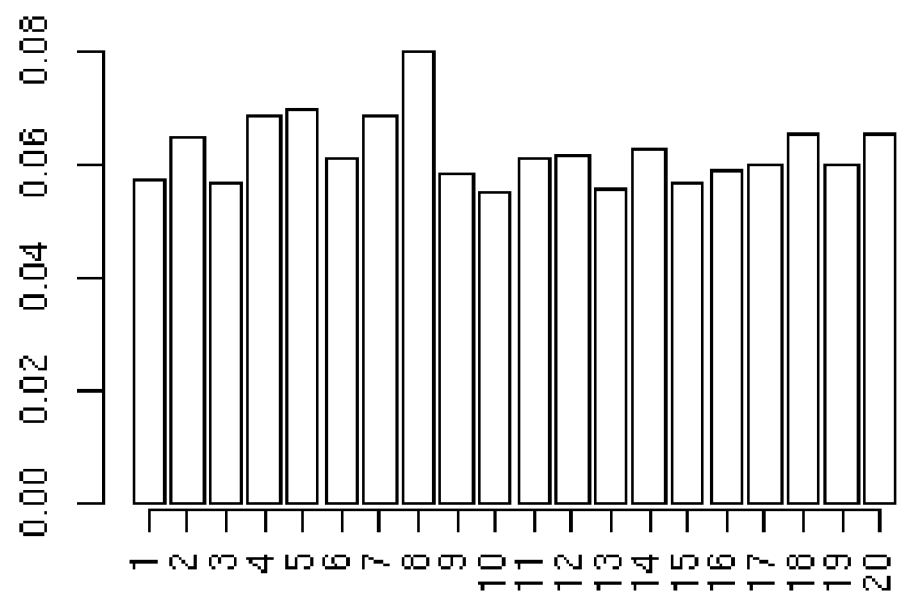
FIG. 25: Bar chart of mad(plier residuals)

Summaries of residuals from fits. A by-product of the PLIER fit is the residuals from the model fit. These can be summarized in various ways to produce quality indicators. The median of the absolute value of residuals, pooled over all features sets, provides a simple array-level summary that will detect some differences in technical variability between arrays. FIG. 25 displays a bar graph, with bar height proportional to mad(plier residual) for the 20 chips we have been using for illustration. Array 8 stands out as the chip with the largest mad(plier residual). Mad(plier residual) is highly correlated with the interquartile range of relative $\log_2$ signal.

Alternatively, the residuals can be combined into standard errors of signal estimates, and these can be summarized over all features sets on the array. The standard error can be normalized, by the median standard error for each feature set, for example, to provide a quality indicator that is slightly more sensitive to differences between arrays (see derivation of NUSE values in the Bioconductor monograph). As in the case of the relative $\log_2$ signal values summaries, the various residual summaries can be confined to various collections of features or feature sets.

ExACT Quality Report. The probe summarization step (exact-probe-summarize command) will generate an optional report file. This text file contains various summary metrics from the CEL file data. It is important to note that the report file results are dependent on the particular analysis parameters used; thus different results can be generated from the same set of CEL files depending on which intensity method, quantification method(s), and probesets are used.

The quality report file includes meta information about the particular analysis run. This information is encoded as lines starting with the pound symbol ('#'). For example, the line starting with '#%cmd=' contains the specific command line parameters used when the report file was generated.

Following the meta information is the summary metrics for each CEL file. The format is a column for each CEL file and a row for each metric with a tab separating each column. This file can be opened within Excel for instance as a tab separated text file. The various quality control metrics reported are as follows with each metric potentially reported multiple times for different subsets of probesets. For example, the AFFX spike control probesets are reported separately (if included in the analysis) and as part of the total.

The following terms are used herein and given the following meanings. Probe Count is the number of probes (features) analyzed. Probeset Count is the number of probesets analyzed. % Probes DABG Detected is the percent of probes with a DABG probe level p-value less than or equal to 0.01. This metric is only reported if the DABG quantification method is selected. % Probesets DABG Detected is the percent of probesets with a DABG probeset level p-value less than or equal to 0.01. This metric is only reported if the DABG quantification method is selected. Mean Probeset PLIER Target Response: The mean PLIER signal estimate. Mean Probeset Abs PLIER Residuals is the mean absolute PLIER probe level residuals. Mean Probeset Abs PLIER RLE is the mean absolute PLIER relative log expression (RLE). This metric is generated by taking the PLIER estimate for a given chip and calculating the difference in log base 2 from the median value of that probeset over all the chips. The mean is then computed from the absolute RLE for all the probesets for a given CEL file.

Positive vs Negative ROC AUC is the area under the curve (AUC) for a receiver operator curve (ROC) comparing the intron controls to the exon controls by applying a threshold to the PLIER signal estimate. The ROC curve is generated by evaluating how well the PLIER signal estimate separates the intron controls from the exon controls. The assumption (which is only valid in part) is that the intron controls are a measure of false positives and the exon controls are a measure of true positives. An AUC of 1 reflects perfect separation whereas as an AUC value of 0.5 would reflect no separation. Note that the AUC of the ROC curve is equivalent to a rank sum statistic used to test for differences in the center of two distributions. These metrics in general (and the RLE, ROC AUC, and Residual metrics specifically) have proven most useful in helping to identify outlier chip results relative to a given data set.

Methods for deriving simple measures from array data, the feature or the feature set level, to assess the quality of array data in terms of comparability are disclosed. It was argued that although comparing arrays in terms of feature intensity level is useful, decisions regarding which arrays to exclude from analysis should be based on signal level data—the data that will be used in downstream analysis. Other measures may also be used to assess quality.

Many of the quality assessment measures will be highly correlated. For the purpose of identifying gross outliers that should be excluded from downstream analysis any of the assessments discussed above will do a good job. Better methods—methods that are sensitive to departures in quality that have impact on particular downstream analyses—must by their very nature be developed on a case by case basis.

CONCLUSION

It is to be understood that the above description is intended to be illustrative and not do not by their details limit the scope of the claims of the invention. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

The invention claimed is:

1. A computer-implemented method for identifying exons that are differentially spliced between at least a first and second sample comprising:
    (a) obtaining an exon intensity measurement for a first exon in a first gene in said first sample and in said second sample;
    (b) calculating a gene level measurement for said first gene in said first sample and in said second sample, wherein the gene level measurement for said first gene is a median normalized intensity value from all exons in said first gene in said first sample and the gene level measurement for said second sample is a median normalized intensity value from all exons in said first gene in said second sample;
    (c) calculating a first normalized intensity measurement for said first exon in said first sample and a second normalized intensity measurement for said first exon in said second sample by dividing the intensity measurements obtained in (a) by the gene level measurements obtained in step (b) wherein the exon intensity in said first sample is divided by the gene level measurement in said first sample and the exon intensity in said second sample is divided by the gene level measurement in said second sample;
    (d) calculating a splicing index measurement for said first exon, wherein the splicing index is equal to the $\log_2$ of the normalized intensity for said first exon in said first sample divided by the normalized intensity for said first exon in said second sample, and wherein the calculating in steps (b), (c) and (d) is performed by a computer comprising a computer software product; and
    (e) identifying said first exon as being differentially spliced if the absolute value of the splicing index obtained in (d) is greater than a threshold value,
    wherein exon array background correction is performed by use of a background probe collection.

2. The method of claim 1 where the threshold value is 1-2.

3. The method of claim 1 wherein the threshold value is 2.

4. The method of claim 1 wherein the normalized intensity measurements of step (c) are obtained using the following equation:

$$n_{i,j,k} = \frac{e_{i,j,k}}{g_{j,k}}$$

where $e_{i,j,k}$ is the exon signal estimate of the i exon, j experiment, and k gene and $g_{j,k}$ is the gene level signal estimate of the j experiment and k gene.

5. The method of claim 4 wherein a first value of $n_{i,j,k}$ is calculated by the computer for a first sample and a second value of $n_{i,j,k}$ is calculated by the computer for a second sample and the splicing index is calculated by the computer by dividing the value of the $n_{i,j,k}$ for said first sample by the $n_{i,j,k}$ for said second sample to obtain a third value and calculating the $\log_2$ of said third value.

6. The method of claim 1 wherein the exon is identified as being overrepresented in said first sample relative to said second sample if the splicing index is greater than zero.

7. The method of claim 1 wherein the exon is identified as being overrepresented in said first sample relative to said second sample if the splicing index is greater than 2.

8. The method of claim 1 wherein the exon is identified as being underrepresented in said first sample relative to said second sample if the splicing index is less than 0.

9. The method of claim 1 wherein the exon is identified as being underrepresented in said first sample relative to said second sample if the splicing index is less than −2.

10. A computer-implemented method for identifying exons that are differentially spliced between at least a first and second sample comprising:
    (a) obtaining an exon intensity measurement for a first exon in a first gene in said first sample and in said second sample;
    (b) calculating a gene level measurement for said first gene in said first sample and in said second sample, wherein the gene level measurement of the first sample is a median normalized intensity value from all exons in said first gene in said first sample and the gene level measurement of the second sample is a median normalized intensity value from all exons in the first gene in the second sample;
    (c) calculating a first normalized intensity measurement for said first exon in said first sample and a second normalized intensity measurement for said first exon in said second sample using the following equation:

$$n_{i,j,k} = \frac{e_{i,j,k}}{g_{i,k}}$$

where $e_{i,j,k}$ is the exon signal estimate of the i exon, j experiment, and k gene and $g_{j,k}$ is the gene level signal estimate of the j experiment and k gene;
    (d) calculating a splicing index measurement for said first exon, wherein a first value of $n_{i,j,k}$ is calculated for a first sample and a second value of $n_{i,j,k}$ is calculated for a second sample and the splicing index is calculated by dividing the value of the $n_{i,j,k}$ for said first sample by the $n_{i,j,k}$ for said second sample to obtain a third value and calculating the $\log_2$ of said third value, and wherein the calculating in steps (b), (c) and (d) is performed by a computer comprising a computer software product; and
    (e) identifying said first exon as being differentially spliced if the absolute value of the splicing index obtained in (d) is greater than a threshold value,
    wherein exon array background correction is performed by use of a background probe collection.

11. The method of claim 10 wherein the threshold value is between about zero and about 2.

12. The method of claim 10 wherein the exon intensity measurements are obtained by hybridizing nucleic acid derived from the sample to an array of probes wherein there is a probeset comprising a plurality of probes for each exon to be interrogated and there are more than 10,000 different probesets.

* * * * *